(12) United States Patent
Davis et al.

(10) Patent No.: US 11,667,966 B2
(45) Date of Patent: Jun. 6, 2023

(54) NANOPORE-BASED SINGLE DNA MOLECULE CHARACTERIZATION, IDENTIFICATION AND ISOLATION USING SPEED BUMPS

(71) Applicant: Roche Sequencing Solutions, Inc., Pleasanton, CA (US)

(72) Inventors: Randall W. Davis, Pleasanton, CA (US); Roger J. A. Chen, Saratoga, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 195 days.

(21) Appl. No.: 17/146,138

(22) Filed: Jan. 11, 2021

(65) Prior Publication Data

US 2021/0207212 A1 Jul. 8, 2021

Related U.S. Application Data

(63) Continuation of application No. 16/386,888, filed on Apr. 17, 2019, now Pat. No. 10,920,271, which is a continuation of application No. 15/435,206, filed on Feb. 16, 2017, now Pat. No. 10,400,278, which is a continuation of application No. 14/471,051, filed on Aug. 28, 2014, now Pat. No. 9,617,593, which is a continuation of application No. 13/333,932, filed on Dec. 21, 2011, now Pat. No. 8,845,880.

(60) Provisional application No. 61/426,322, filed on Dec. 22, 2010, provisional application No. 61/426,323, filed on Dec. 22, 2010.

(51) Int. Cl.
*C12Q 1/6869* (2018.01)
*C12Q 1/6816* (2018.01)
*B82Y 15/00* (2011.01)
*G01N 33/487* (2006.01)
*G01N 27/447* (2006.01)
*C12Q 1/6825* (2018.01)
*B82Y 10/00* (2011.01)

(52) U.S. Cl.
CPC ............ *C12Q 1/6869* (2013.01); *B82Y 15/00* (2013.01); *C12Q 1/6816* (2013.01); *C12Q 1/6825* (2013.01); *G01N 27/447* (2013.01); *G01N 33/48721* (2013.01); *B82Y 10/00* (2013.01); *Y10S 977/924* (2013.01)

(58) Field of Classification Search
CPC combination set(s) only.
See application file for complete search history.

(56) References Cited

U.S. PATENT DOCUMENTS 10,920,271 B2 * 2/2021 Davis .................. G01N 27/447
2010/0331194 A1 * 12/2010 Turner ................. G01N 27/447
438/49

* cited by examiner

Primary Examiner — J. Christopher Ball
(74) Attorney, Agent, or Firm — FisherBroyles, LLP; Jason M. Pass

(57) ABSTRACT

The present invention relates to a method of using nanopores to obtain sequence information of sample DNAs in ss test DNAs. The method comprises using speed bumps to stall the ss test DNAs in the nanopores at random positions of the ss test DNAs to obtain sequence information of each and every nucleotides of the sample DNAs, and to construct the whole sequences of the sample DNAs. The present invention also relates to identification and/or isolation of test DNAs having desired sequence(s) using nanopore detectors facilitated by speed bump.

9 Claims, 18 Drawing Sheets

Specification includes a Sequence Listing.

NANOPORE-BASED SINGLE DNA MOLECULE CHARACTERIZATION, IDENTIFICATION AND ISOLATION USING SPEED BUMPS

CROSS-REFERENCE TO RELATED APPLICATIONS

The present application is a continuation of U.S. patent application Ser. No. 16/386,888, filed Apr. 17, 2019, which is a continuation of U.S. patent application Ser. No. 15/435,206, filed Feb. 16, 2017, now U.S. Pat. No. 10,400,278, which is a continuation of U.S. patent application Ser. No. 14/471,051, filed Aug. 28, 2014, now U.S. Pat. No. 9,617,593, which is a continuation of U.S. patent application Ser. No. 13/333,932, filed Dec. 21, 2011, now U.S. Pat. No. 8,845,880, which claims priority to U.S. Provisional Application Nos. 61/426,322, filed Dec. 22, 2010 and 61/426,323, filed Dec. 22, 2010; each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 25, 2021, is named 04338-004US6_ST25.txt and is 2 kilobytes in size.

FIELD OF THE INVENTION

The present invention relates to a method of DNA sequencing and isolation using nanopore detectors in the presence of speed bumps.

BACKGROUND OF THE INVENTION

A nanopore is a nanometer-scale pore providing the sole pathway for an ionic current. An exemplary nanopore can be created from depositing alpha homolysin onto the surface of a lipid bilayer under electrical stimulus, as described in US Application Publication No. 2011/0193570, which are herein incorporated by reference in their entireties.

Nanopore sequencing has the potential to become a direct, fast, and inexpensive DNA sequencing technology. Ideally, individual nucleotides of a single-stranded (ss) DNA passing through a nanopore will uniquely modulate an ionic current flowing through the nanopore, allowing the record of the current to provide DNA sequence information. However, a common challenge to nanopore sequencing is that the ss test DNA translocation is rapid, and the electrical signals obtained cannot be resolved for reliable DNA sequencing. DNA duplex sections have been used to slow translocation of a ss test DNA to provide more resolvable electrical signals. However, as the currently available methods conduct nanopore detection at about room temperature or higher, a relatively long DNA duplex section is required to stall the ss test DNA in the nanopore.

Thus, there is a need to provide a method to sequence an unknown DNA using nanopore technology.

SUMMARY OF THE INVENTION

One aspect of the invention relates to characterization and identification of a sample DNA using a nanopore detector facilitated by a random speed bump pool.

Another aspect of the invention relates to characterization and identification of multiple sample DNAs using multiple nanopore detectors facilitated by speed bumps.

Another aspect of the invention relates to characterization, identification and isolation of desired sample DNAs using multiple nanopore detectors facilitated by speed bumps.

DETAILED DESCRIPTION OF THE INVENTION

Definitions

Figure 1:
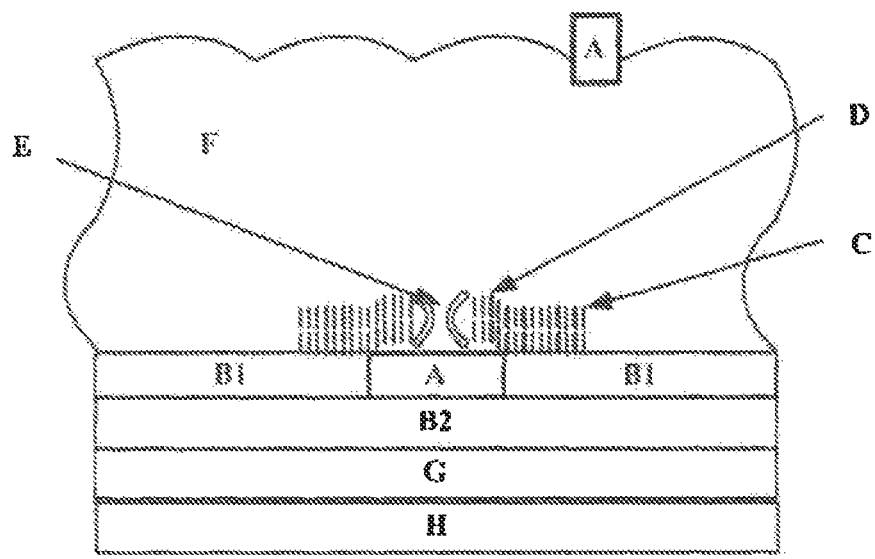
FIG. 1 illustrates an example of a nanopore detector showing: [A] Electrodes; [B1] Treated Hydrophobic/Lipophilic Semiconductor Surface; [B2] Semiconductor substrate containing electronic circuitry; [C] Solvent/Lipid; [D] Lipid Bilayer; [E] Pore; [F] Conductive solution (salt solution); [G] Chip Packaging; and, [H] Peltier device for electronic temperature control.

A sample DNA comprises a DNA of interest, which can be a single-stranded sample DNA (ss sample DNA) or a double-stranded sample DNA (ds sample DNA). The sample DNA can be a natural. DNA obtained from a biological sample or a synthetic DNA. The synthetic DNA may be a DNA obtained by modification of a natural DNA, such as pre-processed. DNA intended for use in DNA identification and/or sequencing. Examples of such pre-processings include, without limitation, enrichment of the sample DNA for desired fragments, paired-end processing, mated pair read processing, epigenetic pre-processing including bisulfide treatment, focused fragment analysis via PCR, PCR fragment sequencing, and short DNA fragment analysis.

A test DNA, as used herein, is a DNA molecule that passes through a nanopore for detection purposes. A test DNA can be a single-stranded test DNA (ss test DNA) and a double-stranded test DNA (ds test DNA). A ss test DNA, as used herein, comprises a section of ss DNA that is to be bound by a speed bump in a method described herein. A ss test DNA may further comprise a sample DNA and other functional moieties (e.g. pre-bulky structure, identifiers and isolation tags).

A pre-bulky structure, as used herein, is an oligonucleotide structure in a DNA molecule which can form a bulky structure under certain conditions. The pre-bulky structure can be a ss DNA or a ds DNA.

A bulky structure, as used herein, is nucleotide structure formed from a pre-bulky structure in a ss test DNA molecule. The bulky structure stalls the test DNA molecule in a nanopore at a working condition until the working condition is changed to another condition wherein the bulky structure is converted to the pre-bulky structure or other structures that cannot stall the test DNA molecule any more. Examples of bulky structures include, without limitation, 2-D and 3-D structures such as DNA duplex structures, DNA hairpin structures, multi-hairpin structures and multi-arm structures.

A nanopore, as used herein, is a pore of nanometer dimensions formed by a pore-forming protein being inserted into a membrane. Typically, the membrane is an electrically insulating lipid bilayer membrane. Pore-forming proteins, such as alpha hemolysin and MspA porin, are inserted into the membrane to form nanopores through the protein molecule and the membrane. Electrophysiology measurements can be taken by measuring the ionic current passing through a nanopore as a voltage is applied across the membrane. A nanopore can be utilized as a molecule detector by monitoring the ionic current variation in response to the passage of the molecule through the nanopore. A nanopore can be a synthetic, man-made, biologically altered, wild-type biological nanopore, or a combination thereof.

A speed bump, as used herein, is an oligonucleotide molecule that forms a complex with a binding segment of a test DNA molecule. When the test DNA molecule goes through a nanopore under an electric potential, the complex formed between the speed bump and the binding segment stalls the test DNA molecule in the nanopore for a dwelling time long enough for the nanopore detector to obtain structure information of the test DNA molecule. After the dwelling time, the complex dissociates and the test DNA molecule moves forward through the nanopore.

An identifier, as used herein, is a known structure in a test DNA that can be detected or identified by the method described herein. Examples of identifiers include, without limitation, direction identifiers, reference signal identifiers, sample source identifiers, and sample identifiers. The identifiers may comprise one or more nucleotides or structures that provide distinctive electrical signals that are easily identified. Examples of such nucleotides and structures include, without limitation, isodG, isodC, methylated nucleotides, locked nucleic acids, universal nucleotides, and abasic nucleotides. In certain embodiments, an abasic nucleotide provides a stronger signal than a primary nucleotide. Thus, the electrical signal detected by a nanopore for a sequence comprising both abasic nucleotides and primary nucleotides will provide a signal more intense than the electrical signal obtained from primary nucleotide only sequences. For example, a 4~5 base sequence comprising about 25% abasic nucleotides may provide a signal more than twice as strong as a 4~5 base sequence comprising only primary nucleotides. The more abasic nucleotides the sequence have, the stronger electrical signal the sequence. Thus, identifiers may provide electrical signals of a desired intense (e.g. about twice, about 3, 4, 5, 6, 7, 8, 9, or about 10 times stronger than that of primary oligonucleotides having the same length) by changing the amount of abasic nucleotides in the identifier sequences.

Figure 9:
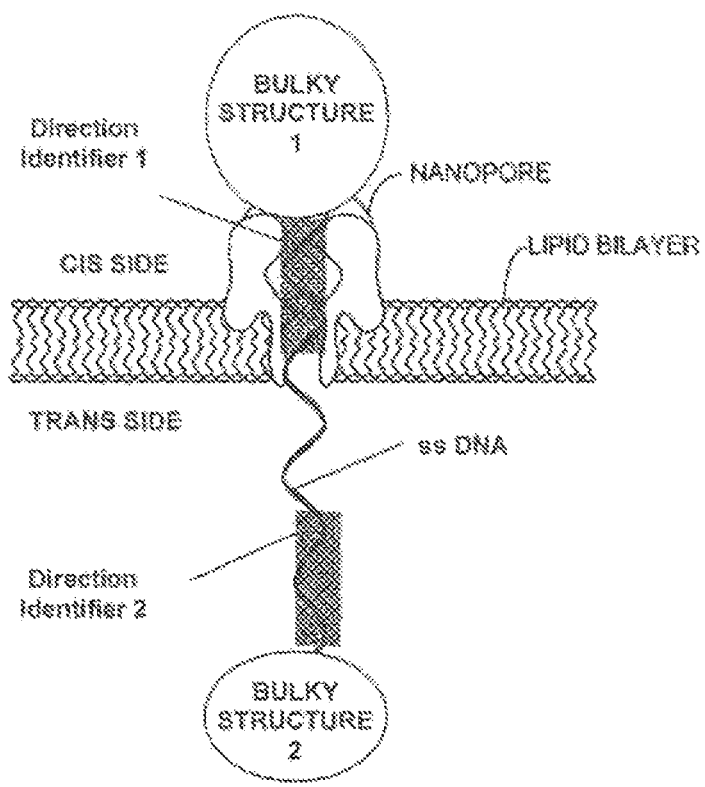
FIG. 9 illustrates detection of direction identifier in a ss test DNA trapped in a nanopore bound by two bulky structures

Direction identifier, as used herein, is a known sequence positioned 0, 1, 2, 3, 4, 5, 6, 7, 8, 9, 10, 11, 12, 13, 14, 15, 16, 17, 18, 19, or 20 bases from a bulky structure formed from a pre-bulky structure (the shaded section in the ss test DNA molecule, FIG. 9). When the bulky structure is properly formed, it will stop the ss test DNA molecule from flowing through a nanopore that the ss test DNA molecule is in. Thus, when the bulky structure is stopped inside the nanopore, a set of electrical signals will be obtained, which provide sequence information of the sequence that is in front of the bulky structure and the first basepair of the bulky structure, in the flow direction of the ss test DNA molecule. When the sequence is known, such electrical signals can:

1) verify that the pre-bulky structure has properly formed into the bulky structure such that the bulky structure stops the ss test DNA molecule from flowing through the nanopore;

2) indicate that the ss test DNA molecule has reached one end of the single strand section of the ss test DNA, and 3) serve as a reference or calibration read to base line other electrical signals obtained in the same nanopore.

In certain embodiments, the direction identifier comprises one or more nucleotides or structures that provide distinctive electrical signals that are easily identified. Examples of such nucleotides and structures include, without limitation, isodG, isodC and abasic nucleotides.

Reference signal identifier, as used herein, is a known sequence in a test DNA, when detected or identified by the method described herein, serves as a reference or calibration read to base line other electrical signals obtained in the same nanopore.

Sample source identifier, as used herein, is a known sequence in a test DNA, when detected or identified by the method described herein, is used to identify the source that the sample DNA is from.

Sample identifier, as used herein, is a known sequence in a test DNA, when detected or identified by the method described herein, is used to identify the individual sample DNA.

A known speed bump is a speed bump that specifically binds to a known sequence in a ss test DNA. Because the binding segment on the ss test DNA (the known sequence) is known, the speed bump structure can also be known (e.g. complementary to the known sequence on the ss test DNA).

A random speed bump pool, as used herein, comprises a collection of speed bumps that can bind to all sections of a test DNA molecule or a fragment thereof. An example of random speed bump pool comprises oligonucleotides having universal nucleobases which base-pair with all primary nucleobases (A, C and G). Another example of random speed bump pool comprises oligonucleotides of a given length having all possible combinations of primary nucleobases. Another example of random speed bump pool comprises oligonucleotides of a given length having every possible combination of primary nucleobases and universal nucleobases, Another example of random speed bump pool comprises speed bumps having universal nucleobases at designated positions and all combinations of primary nucleobases at the other positions. Another example of random speed bumps is a combination of ss speed bumps, which form duplex sections with ss test DNA, and the duplex sections have about the same melting temperatures. These ss speed bumps may have the same or different lengths, and/or the same or different nucleotides.

"About," as used herein, refers to +/−10% of the recited value.

The present invention is directed to a method for detecting and/or identifying a sequence in a test DNA using a nanopore detector. The DNA sequence is trapped in the nanopore by one or two bulky structures formed at the end(s) of the DNA sequence, so that the same test DNA can be read multiple times by the same nanopore detector. Furthermore, each bulky structure can be bound to the 5' end or the 3' end to thread the sample DNA into the pore in a known direction, Known speed bumps are used to bind to known sequences in the test DNA for the detection/identification of the known sequences. This method can be used to detect whether the test DNA has correctly threaded into the nanopore, which sample source the test DNA is from, and individually identify the test DNA trapped in the nanopore. Furthermore, the test DNA may, further comprise a reference signal indicator to generate electrical signals that can be used as reference of calibration for other electrical signals obtained form the same nanopore. Furthermore, multiple test DNAs can be analyzed by multiple nanopores at the same time for efficient and simultaneous sequencings and characterizations. The multiple nanopores can be individually addressable and individually applied desired electric potential, Thus, multiple test DNAs can be analyzed simultaneously first to identify the DNAs having one or more desired known sequences. The DNAs that do not have the desired known sequence can be released without further characterizations. The DNAs having the desired known sequences can be further characterized, and optionally isolated and concentrated as described herein.

A random speed bump pool is used to bind to the test DNA or a fragment thereof in a random fashion. Thus, each and every nucleotide of the test DNA or the fragment thereof will be stalled in the nanopore for a time long enough to collect the nucleotide sequence information. The nucleotide sequence of the test DNA or the fragment thereof can be identified by taking all the sequence information obtained together. The test DNA may further comprise known structures such as direction identifiers, reference signal identifiers, sample source identifiers, sample identifiers to provide information, e.g. formation of the bulky structures, source of the test DNA, and identification of the test DNA. The test DNA may further comprise an isolation tag to isolate and concentrate the test DNA. In certain embodiments, multiple test DNAs are detected/identified by multiple nanopores (e.g. in a nanopore array). The method described herein can be applied to each test DNA detected/identified. The nanopores can be individually addressed and controlled to selectively detect/identify/collect/concentrate test DNA(s) therein.

FIG. 1 shows an example of a nanopore detector having temperature control, which is prepared according to US Application Publication No. 2011/0193570. The nanopore detector comprises electrodes (A), a treated semiconductor hydrophobic surface (B1) in which is embedded a conductive electrode (A) that is connected to electrical circuitry in a semiconductor substrate (B2), a layer of lipid material (C) created over an electrode (A) and a small portion of the hydrophobic surface closeby (B1), and a nanopore (D) inserted in the lipid material through a conductive salt solution (F). A sample detected goes through the pore (E) in the nanopore. The semiconductor chip sensor is placed in package (G) and this, in turn, is in the vicinity of a Peltier device or temperature control element (H). Multiple nanopore detectors can be created to form a nanopore array.

Figure 2:
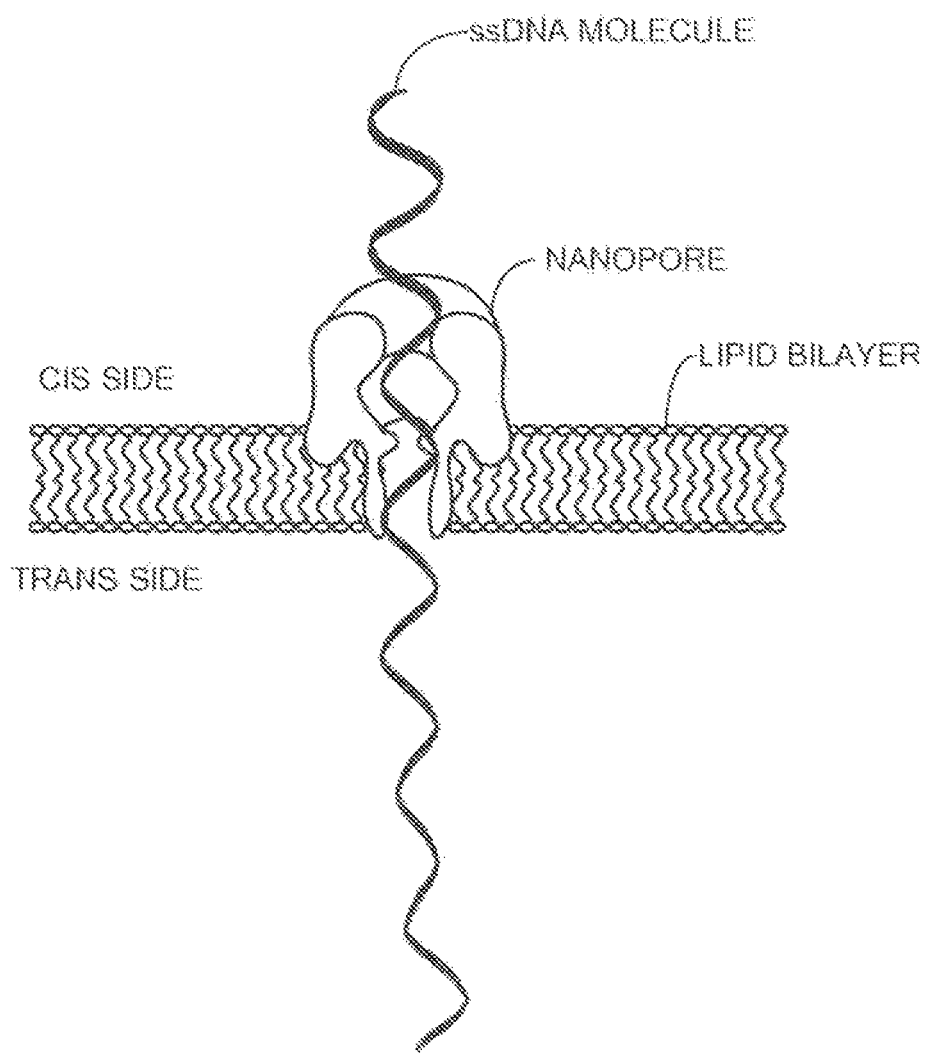
FIG. 2 illustrates the passage of a single stranded (ss) test DNA molecule through a nanopore.

As illustrated in FIG. 2, a single-stranded (ss) DNA molecule can go through a nanopore under an applied electric potential. A set of electrical signals corresponding to the brief blockages of ion flow through the nanopore by the ss test DNA molecule is detected as the ss test DNA molecule is threaded through the nanopore. In the absence of speed bumps or bulky structures, the ss test DNA molecule encounters little resistance and travels through the nanopore too quickly for electrical signals to be reliably recorded for sequencing of the ss test DNA.

Figure 3:
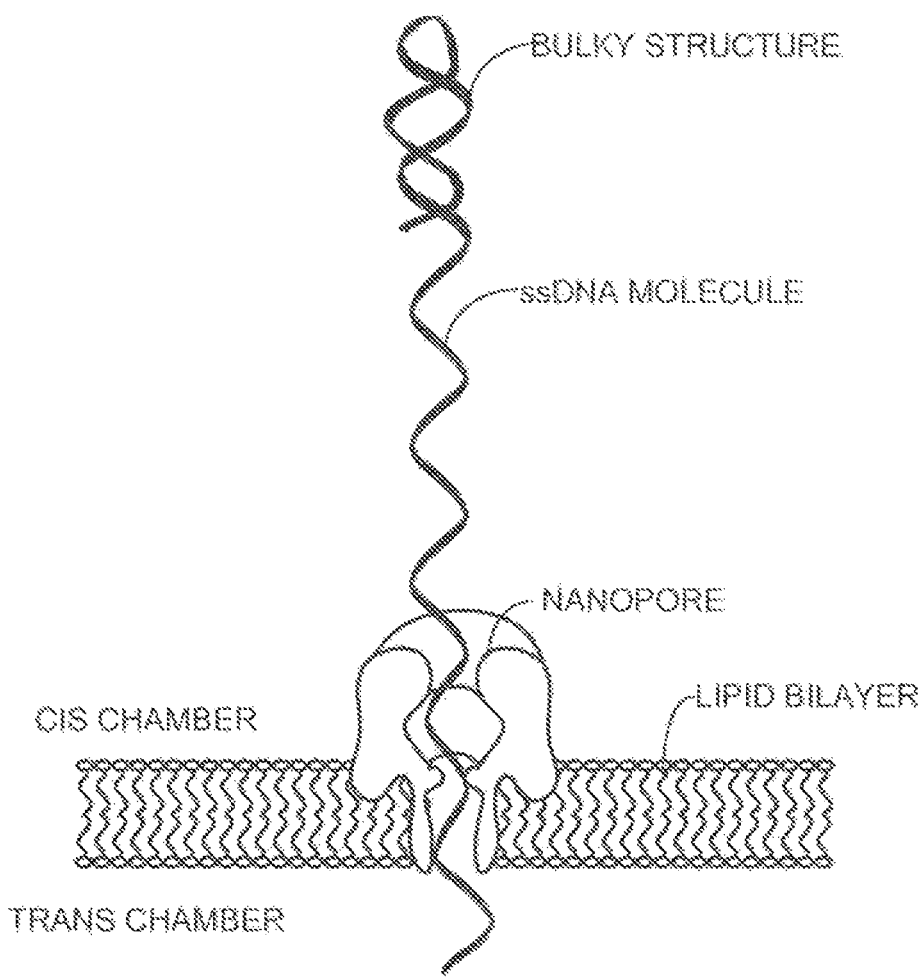
FIG. 3 illustrates a bulky structure formed at the trailing end of a ss test DNA molecule to stall the passage of the ss test DNA through a nanopore.

Bulky structures (BSs) have been used to stop the passage of a ss test DNA through a nanopore. FIG. 3 illustrates a trailing end BS used to stop the passage of a ss test DNA molecule through a nanopore. The BS can be a hairpin structure formed at one end of the ss test DNA by wrapping the trailing end of the ss test DNA upon itself. Typically, the ss test DNA can be threaded through the nanopore under an applied electric potential until the bulky hairpin structure reaches the entrance of the nanopore. Since the hairpin structure is larger than the diameter of the nanopore, the ss test DNA is stalled in the nanopore long enough to obtain a set of electrical signals of the ss test DNA. However, the electrical signals obtained reflects the structure of only a portion of the DNA that is in front of the hairpin or in front of the specific duplex region and therefore in or near the constriction area of the nanopore.

Figure 4:
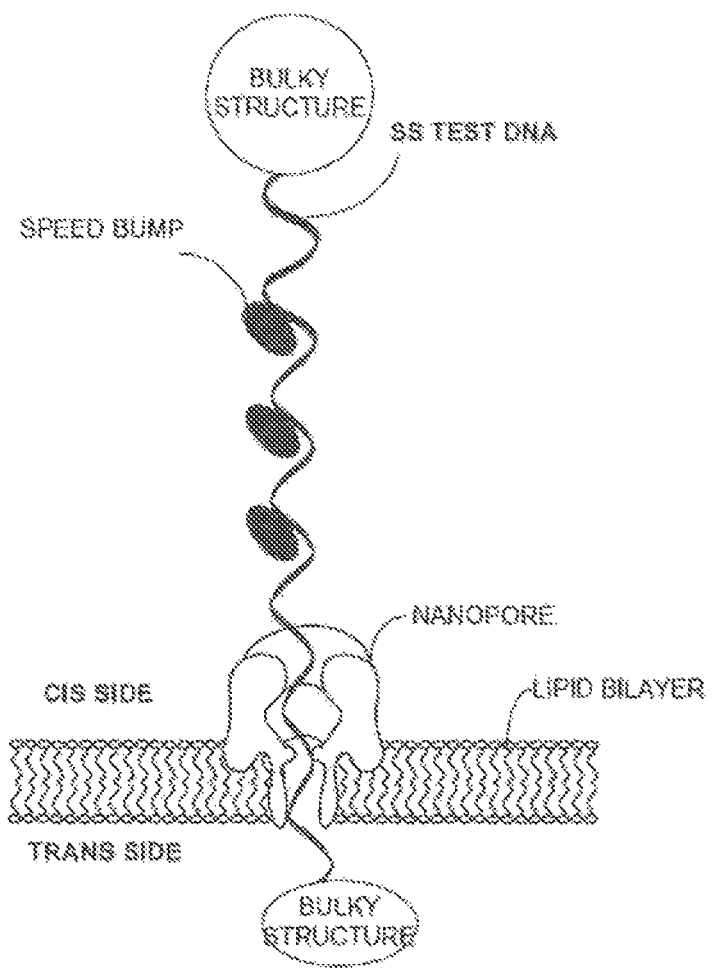
FIG. 4 illustrate multiple speed bumps bound to a ss test DNA molecule, wherein the ss test DNA is trapped in a nanopore by having bulky structures on both ends.

FIG. 4 illustrates a ss test DNA trapped in a nanopore by two bulky structures. The nanopore detection is carried out at a working temperature that may be lower than room temperature so that one or more shorter DNA duplex sections can be formed between speed bumps and the ss test DNA (speed bump-test DNA duplex segments). The speed bump-test DNA duplex segment stalls the ss test DNA for a sufficient dwelling time to obtain sequence information of the ss test DNA segment in front of the speed bump-test DNA duplex segment and the first basepair of the speed bump-test DNA duplex segment in the flow direction of the ss test DNA. Then the speed bump-test DNA duplex segment dissociate and the ss test DNA moves forward through the nanopore until stalled by another speed bump-test DNA duplex segment or stopped by a bulky structure on one end of the ss test DNA. Once the ss test DNA reaches one end, the electric potential can be optionally at a reduced value or a reversed polarity to move the ss test DNA to a reversed direction and repeat the process as desired.

Figure 5:
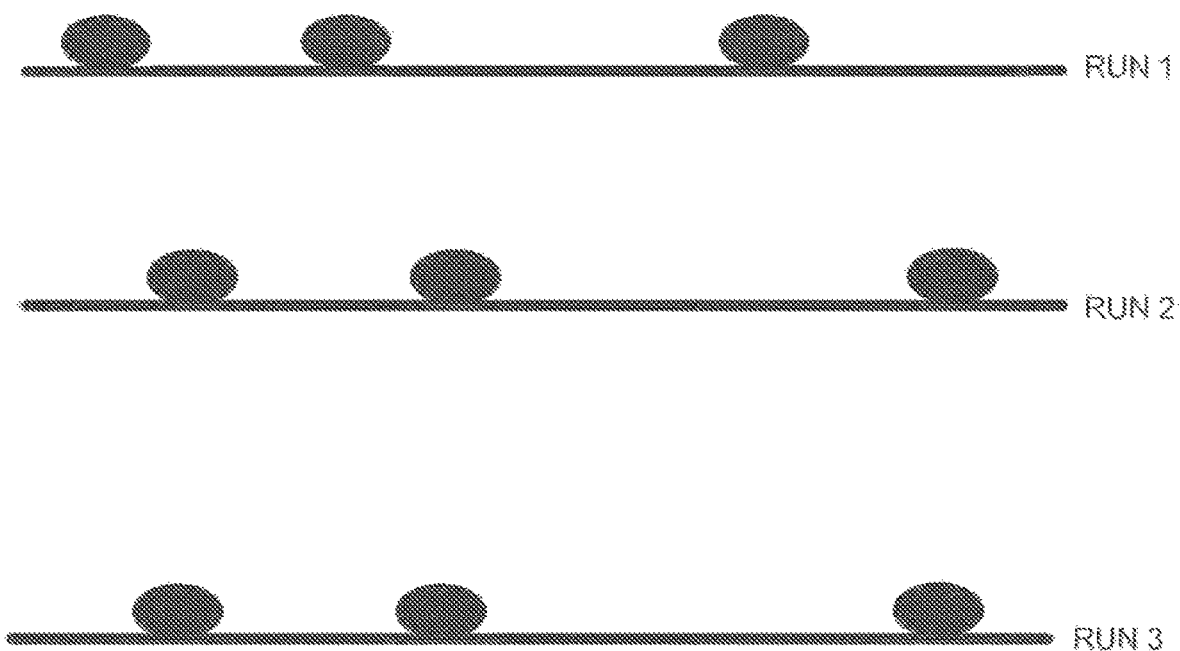
FIG. 5 illustrates different binding patterns achieved by contacting a ss test DNA with a random speed bump pool.
Figure 6:
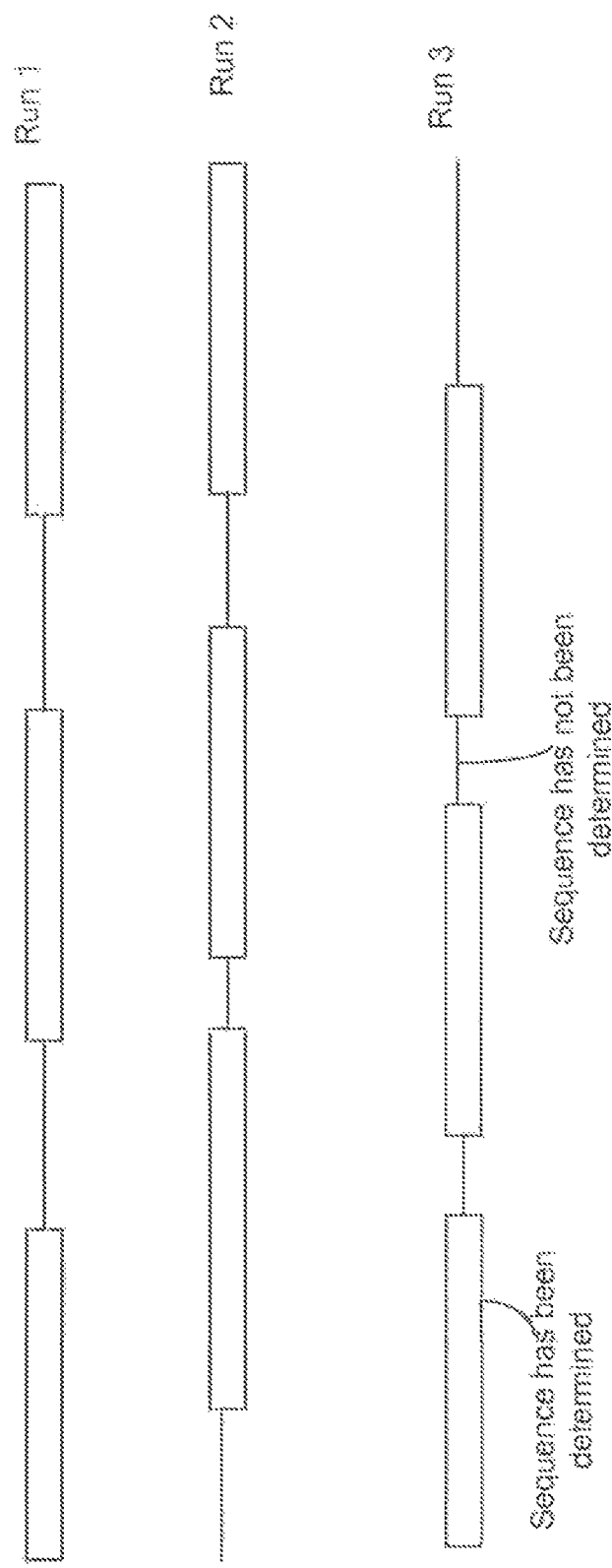
FIG. 6 illustrates different sequence information patterns achieved by randomly stalling a ss test DNA in a nanopore to obtain sequence information.

When the ss test DNA has an unknown sequence e.g. sample DNA), a random speed bump pool can be constructed to bind to random sections of the ss test DNA. As every section of the ss test DNA can be bound by at least one speed bump in the random speed bump pool, the binding patterns achieved by contacting a ss test DNA with a random speed bump pool each time can be random (FIG. 5). Thus, the segments whose sequence information is obtained are also random for each run (FIG. 6). However, repeating the process as described supra allows each and every nucleotide of the unknown sequence to be identified by the nanopore detector. Thus, the whole unknown sequence can be constructed by overlapping the obtained sequence information of random sections of the ss test DNA.

Figure 7:
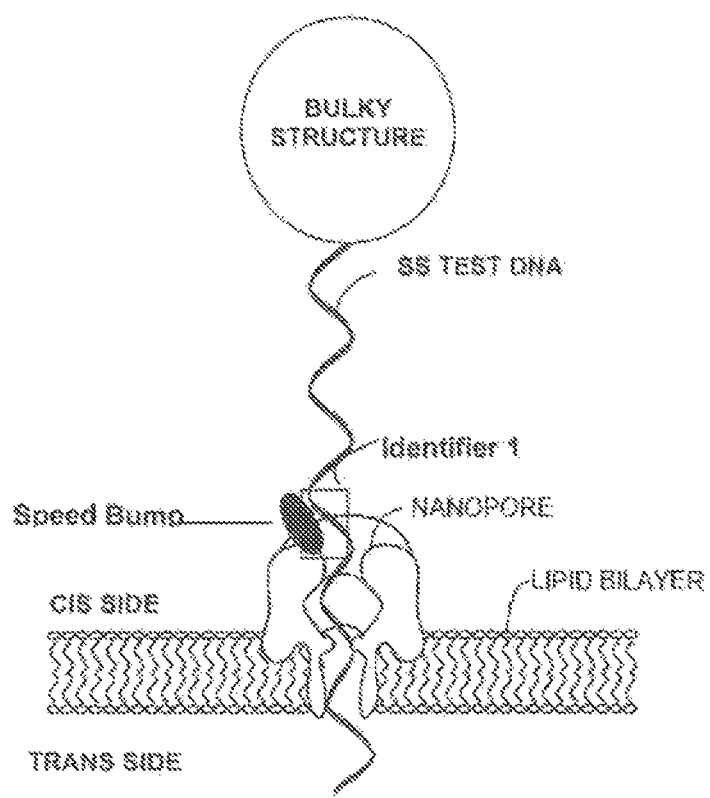
FIG. 7 illustrates a speed bump bound to a ss test DNA having a bulky structure at a first end to stall its passage through a nanopore.
Figure 8:
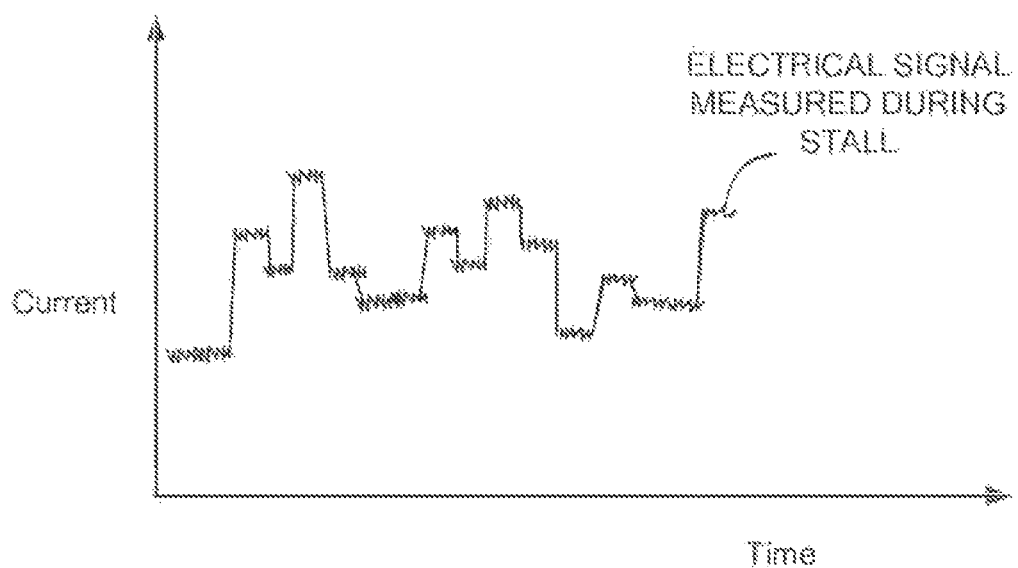
FIG. 8 illustrates multiple sets of electrical signals obtained by a nanopore detector according to the present invention.

When the ss test DNA comprises one or more known sequences (identifiers), the method described herein can also be used to detect the presence of one or more identifiers and/or to identify a sequence on the ss test DNA that is in front of the identifier in the flow direction of the ss test DNA. The ss test DNA can have BS on only one end (FIG. 7) or both ends as described supra. The nanopore detector is operated at a working temperature lower than room temperature. A speed bump pool comprises speed bumps that can bind specifically to the identifier (e.g. identifier 1, FIG. 7) to form a speed bump-identifier duplex segment is used. The speed bump-identifier duplex segment stalls the ss test DNA and a set of electrical signals are obtained. These signals can be characterized to show presence of the identifier or to identify the sequence of the segment before the identifier in the flow direction of the ss test DNA. An example of such electrical signals is shown in FIG. 8.

Design and Construction of Test DNAs from a Sample DNA

In one embodiment, a sample DNA is linked with various functional moieties to facilitate nanopore sequencing and/or identifications. Examples of functional moieties include, without limitation, pre-bulky structures and identifiers as described supra, and isolation tags to facilitate isolation and enrichment of the sample DNA. The functional moieties optionally comprise one or more nucleotides.

As used herein, a nucleotide can be a primary nucleotide or a nucleotide analog. A primary nucleotide is deoxyadenosine mono-phosphate (cAMP), deoxycytidine mono-phosphate (dCMP), deoxyguanosine mono-phosphate (dGMP) or deoxythymidine mono-phosphate (dTMP). A nucleotide analog is an analog or mimic of a primary nucleotide having modification on the primary nucleobase (A, C, G and T), the deoxyribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-difluro-toluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The sample DNA may be a synthetic DNA or a DNA obtained from a biological sample. In one embodiment, the sample DNA has 1 to about 100,000 bases, 1 to about 10,000 bases, 1 to about 1,000 bases, 1 to about 500 bases, 1 to about 300 bases, 1 to about 200 bases, 1 to about 100 bases, about 5 to about 100,000 bases, about 5 to about 10,000 bases, about 5 to about 1,000 bases, about 5 to about 500 bases, about 5 to about 300 bases, about 5 to about 200 bases, about 5 to about 100 bases, about 10 to about 100,000 bases, about 10 to about 10,000 bases, about 10 to about 1,000 bases, about 10 to about 500 bases, about 10 to about 300 bases, about 10 to about 200 bases, about 10 to about 100 bases, about 20 to about 100,000 bases, about 20 to about 10,000 bases, about 20 to about 1,000 bases, about 20 to about 500 bases, about 20 to about 300 bases, about 20 to about 200 bases, about 20 to about 100 bases, about 30 to about 100,000 bases, about 30 to about 10,000 bases, about 30 to about 1,000 bases, about 30 to about 500 bases, about 30 to about 300 bases, about 30 to about 200 bases, about 30 to about 100 bases, about 50 to about 100,000 bases, about 50 to about 10,000 bases, about 50 to about 1,000 bases, about 50 to about 500 bases, about 50 to about 300 bases, about 50 to about 200 bases, or about 50 to about 100 bases.

Pre-Bulky Structures

In one embodiment, a ss test DNA comprises a first pre-bulky structure (PB1) on a first end that can form a first bulky structure (BS1) under a first condition and a second pre-bulky structure (PB2) on a second end that can form a second bulky structure (BS2) under a second condition. In certain embodiments, P131 comprises ss DNA segments that can form BS1 under the first condition. A first condition can be a first temperature T1, which can be about room temperature to 70° C., about 40° C. or higher, about 30° C. or higher, about 25° C. or higher, about 20° C. or higher, or about 15° C. or higher. In certain embodiments, the first condition can be T1 and the presence of a first ligand that can bind to PB1 to form BS1. Examples of the first ligand include, without limitation, antisense oligonucleotide to PB1, other compounds to facilitate formation of BS1 (e.g. compounds that can form a binding-pair with a ligand, wherein the ligand is attached to PB1. Examples of such biding-pairs include, without limitation, antibody-antigen, and biotin-streptavidin system), and combinations thereof through covalent and/or noncovalent interactions. Wherein BS1 is a DNA 2-D or 3-D structure (e.g. duplex, hairpin structure, multi-hairpin structure and multi-arm structure), the melting temperature of BS1 (Tm1) is 15° C. or above, about 20° C. or above, about 25° C. or above, about 30° C. or above, about 35° C. or above, about 40° C. or above, or about 50° C. or above.

PB2 forms BS2 under a second condition. In certain embodiments, PB2 is a ss DNA segment that can form BS2 (e.g. DNA duplex, hairpin structure, multi-hairpin structure and multi-arm structure) under the second condition. A second condition can be a second temperature T2, it is about −5 to about 50° C., about 40° C. or higher, about 30° C. or higher, about 25° C. or higher, about 20° C. or higher, about 15° C. or higher, about 10° C. or higher, or about 5° C. or higher. In certain embodiments, T2 is about at least 5° C. lower, preferably at least about 10° C. lower or at least about 20° C. lower than T1. In certain embodiments, the second condition can be T2 and the presence of a second ligand that can bind to PB2 to form BS2. Examples of the second ligand include, without limitation, antisense oligonucleotide to PB2, other compounds to facilitate formation of BS2, (e.g. compounds that can form a binding-pair with a ligand, wherein the ligand is attached to PB2. Examples of such biding-pairs include, without limitation, antibody-antigen, and biotin-streptavidin system), and combinations thereof through covalent and/or noncovalent interactions, Wherein BS2 is a DNA 2-D or 3-D structure (e.g. duplex, hairpin structure, multi-hairpin structure and multi-arm structure), the inciting temperature of BS2 (Tm2) is about 5~about 10° C., about 10~about 20° C., about 20~about 30° C., or about 20~about 50° C.

In certain embodiments, PB1 and/or PB2 comprise(s) structures that are non-binding to speed bumps in the speed bump pool. Examples of such structures include, without limitation, nucleotide analogs comprising non-binding bases such as IsodG, IsodC and abasic site.

Identifiers

In certain embodiments, a ss test DNA further comprise(s) functional moieties such as identifiers and isolation tags. In certain embodiments, when the ss test DNA is contacted with a random speed bump pool, identifier and isolation tags are constructed such that they will not be bound by the random speed bump pool. For example, an identifier segment can have isodG and isodC bases which preferably bind to each other. If speed bumps of the random speed bump pool do not have isodG or isodC base, speed bumps from the random speed bump pool will more preferably bind to sections of the ss test DNA that is outside of the identifier segments. Thus, fewer electrical signals will be collected relating to the sequence information of the identifier, which makes the collected electrical signals easier to characterize.

Examples of identifiers include, without limitation, direction identifiers, reference signal identifiers, sample source identifiers and sample identifiers.

A ss test DNA may have only one bulky structure on one end (FIG. 7), or two bulky structures on both ends (FIG. 9). One direction identifier will be positioned closely (e.g. 0, 1, 2, 3, 4, 5, 6, 7, 8, 9, 10, 11, 12, 13, 14, 15, 16, 17, 18, 19, or 20 bases) to each bulky structure in the ss test DNA. The direction identifiers for different bulky structures can be the same or different.

When the ss test DNA has two bulky structures and two direction identifiers, other identifiers can be positioned between the two direction identifiers. When the ss test DNA has only one bulky structure on one end and one direction identifier, other identifiers can be positioned further away from the bulky structure compared to the direction identifier.

Other identifiers include, without limitation, reference signal identifier serves as a reference or calibration read to base line other electrical signals obtained in the same nanopore; sample source identifiers used to identify the source of the sample DNA; and sample identifiers used to identify individual sample DNAs.

Figure 10:
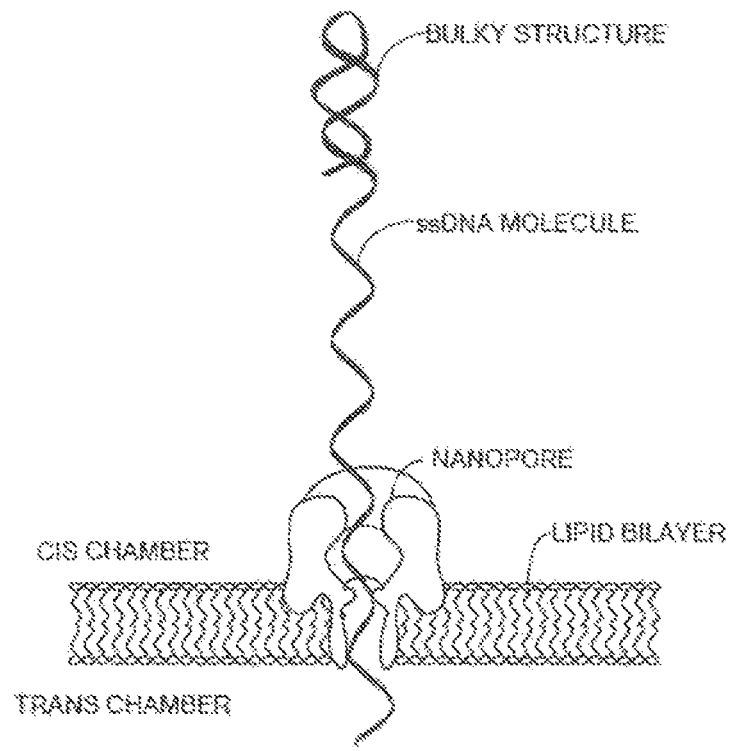
FIG. 10 illustrates detection of an identifier by an identifier-specific speed bump.

Because the structures of the identifiers are known, an identifier can be detected and/or identified by contacting an identifier-specific speed bump with the ss test DNA. If the ss test DNA comprises the identifier of interest, an identifier-specific speed bump duplex section will be formed, which will stall the ss test DNA in the nanopore. A set of electrical signals will be obtained while the ss test DNA is stalled in the nanopore, which can be used to indicate the formation of the speed bump-identifier duplex section (identifier, FIG. 10) and/or identify the sequence that is in front of the identifier-speed bump duplex and the first basepair of the identifier-speed bump duplex, in the flow direction of the ss test DNA molecule (shaded section, FIG. 10). FIG. 10 shows the situation in a ss test DNA having only one bulky structure. The same method can be used when the ss test DNA has bulky structures on both ends.

In certain embodiments, the identifiers and/or identifier-specific speed bumps and/or the sequence in front of the identifier in the flow direction of the ss test DNA molecule comprise one or more nucleotides or structures that provide distinctive electrical signals that are easily identified. Examples of such nucleotides and structures include, without limitation, nucleotides comprising isodG or isodC, abasic nucleotides, methylated nucleotides, etc.

Isolation Tags

An isolation tag is a structure that can form a binding-pair with a ligand, wherein the ligand is further modified to facilitate concentration or isolation thereof. Examples of such biding-pairs include, without limitation, antibody-antigen, and biotin-streptavidin system. Examples of further modifications to facilitate concentration or isolation include, without limitation, attachment of the ligand to a magnetic bead that can be easily concentrated and/or isolated.

In certain embodiments, more than one functional moieties may overlap with each other or serve for more than one function.

Figure 11:
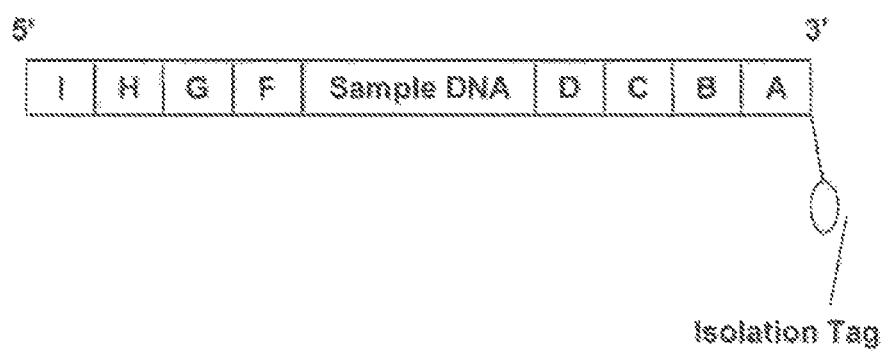
FIG. 11 illustrates an example of a ss test DNA comprising a sample DNA and multiple functional moieties.

An example of a ss test DNA comprising multiple functional moieties (segments A, B, C, D, F, G, H, and I, FIG. 11) and a sample DNA is shown in FIG. 11.

Segment I may serve as a pre-bulky structure and forms a bulky structure with a complementary strand thereof or by self-folding into a structure (e.g. DNA hairpin structures, multi-hairpin structures and multi-arm structures), and segment H or a fragment thereof can serve as a direction identifier. Alternatively, segment I can form a hairpin with segment H under certain conditions. Thus, in this case, a pre-bulky structure is segments I and H. Segment G or a fragment thereof can serve as a direction identifier.

Segment F, G, and H, or a fragment thereof can be a reference signal identifier, a sample identifier, a sample source identifier. Alternatively, segments F, G and H together can be an identifier, or any fragment thereof can also serve as an identifier described supra. Similar situations apply to segments A, B, C and D on the 3' end. An Isolation Tag can be placed on the 3' end or on the 5' end, and it can be linked to the 3' terminal or 5' terminal nucleotide, or to any nucleotide on segments A, B, C, D, F, G, H and I, as long as it does not interfere with the binding of speed bump to the ss test DNA, function of nanopore, or formation of bulky structure.

Construction of ss Test DNA Comprising Sample DNA and One or More Functional Moieties A test DNA comprising sample DNA and one or more functional moieties is constructed by ligating the sample DNA with other segments as desired using conventional organic and/or biological methods can be designed as described supra The ss test DNA shown in FIG. 11 can be formed by linking multiple functional moieties to a sample DNA using conventional ligation methods (e.g. formation of covalent bonds (e.g. ligase assisted ligation or other covalent bonds, wherein the ligation can be accomplished by paired end sequencing chemistry, blunt-ended DNA ligation, and/or sticky-end ligation) or non-covalent interactions).

Figure 12:
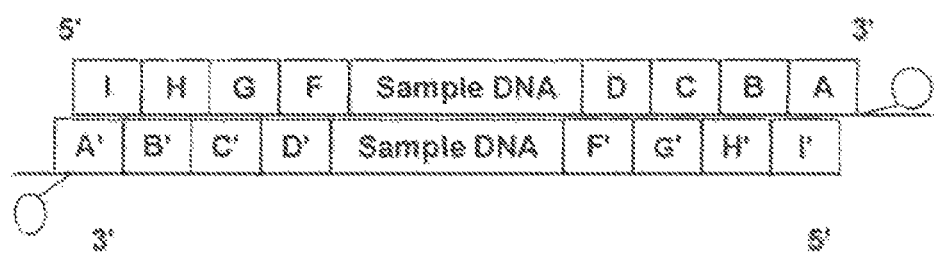
FIG. 12 illustrates an example of a ds test DNA comprising a sample DNA and multiple functional moieties.

In certain embodiments, sample DNA obtained is a double-stranded (ds) sample DNA. The ds sample DNA can be ligated with one or more ds functional moieties (e.g. ds PB1 (Segments I&H-Segments A'&B', FIG. 12), ds PB2 (Segments B&A-Segments H'&I, FIG. 12), ds identifiers (e.g. (Segments G&F-Segments C'&D', and Segments D&C-Segments F'&G', FIG. 12), etc.) using conventional ligation methods (e.g. ligase assisted ligation following blunt end, dangling end, and/or linker ligation; mate-paired and end-paired protocols.) (FIG. 12). The functional moieties can be ligated to the sample DNA all in one step, or sequentially, or all functional moieties on one end of the sample DNA are constructed together first and then ligated to the end of the sample DNA. Examples of the conventional ligation methods includes, without limitation, ligase assisted ligation following blunt end, dangling end, and/or linker ligation; paired end sequencing protocols; mate-paired and end-paired protocols. The obtained ds DNA is then denatured to provide ss test DNA using conventional methods (e.g. heated to denature the ds DNA).

In certain embodiments, the sample DNA obtained is a ds sample DNA, and is linked to one or more ds functional moieties (e.g. ds PB1, ds PB2, ds identifiers etc.) via covalent bonds other than the phosphodiester bonds. Examples of such linkage include, without limitation, the linkage in glycol nucleotides, morpholinos, and locked nucleotides.

In certain embodiments, the sample DNA obtained is a ss sample DNA, and its complementary strand can be created to anneal with the ss sample DNA to form a ds sample DNA using conventional methods, and then ligate to one or more ds functional moieties as described supra.

In certain embodiment, a ss sample DNA is linked to one or more ss functional moieties (e.g. ss PB1, ss PB2, ss identifiers etc.) using ligase assisted ligation. In certain embodiments, a ss sample DNA is linked to one or more ss functional moieties via covalent bonds other than the phosphodiester bonds. Examples of such linkage include, without limitation, the linkage in glycol nucleotides, morpholinos, and locked nucleotides.

In certain embodiment, the sample DNA obtained is a ds sample DNA and can be denatured to provide a ss sample DNA to be linked to one or more ss functional moieties as described supra.

In certain embodiments, the functional moieties are linked by cleavable bonds such that one or more individual functional moieties can be cleaved from the ss test DNA. In one embodiment, a bulky structure can be removed from a ss test DNA by cleaving a functional moieties positioned between the sample DNA and the bulky structure. Then, the ss test DNA can be released from the nanopore it is in by applying an electric potential to move the ss test DNA through the nanopore in the direction at which it is no longer stopped by the cleaved bulky structure.

In certain embodiments, desired functional moieties are linked at a desired end (3' or 5') of the sample DNA, such that the test DNA obtained thereof can be threaded into the nanopore at a desired direction (e.g. from 3' end or from 5' end).

Identification of a Sample DNA Using a Random Speed Bump Pool

One aspect of the invention relates to a method of identifying a sample DNA sequence comprising:
(A1) providing a double-stranded (ds) sample DNA;
(A2) ligating a first pre-bulky (PB1) structure to a first end of the ds sample DNA, and ligating a second pre-bulky (PB2) structure to a second end of the ds sample DNA,
(A3) denaturing the ds sample DNA of A2 to a ss test DNA,
(B1) forming a first bulky structure (BS1) from PB1 on the first end of the ss test DNA at a first temperature,
(B2) applying a first electric potential to flow the ss test DNA through a nanopore,
(B3) forming a second bulky structure (BS2) from PB2 on the second end of the ss test DNA at a second temperature,
(B4) optionally applying another electric potential to reverse the flow of the ss test DNA until the ss test DNA is stopped by BS2 before the constriction area of the nanopore,
(B5) contacting a random speed bump pool with the ss test DNA to form a speed bump-ss test DNA complex having at least one speed hump-ss test DNA duplex segment at a working temperature,
(B6) applying a third electric potential to flow the speed bump-ss test DNA complex through the nanopore until a first speed bump-ss test DNA duplex segment is stopped before the constriction area of the nanopore,
(B7) obtaining a first set of electrical signals when the first speed bump-ss test DNA duplex segment is stalled inside the nanopore for a dwelling time, and characterizing the nucleotide sequence that is in front of the first speed bump-ss test DNA duplex segment and the first basepair of the first speed bump-ss test DNA duplex segment, in the flow direction of the ss DNA,
(B8) dissociating the first speed bump-ss test DNA duplex segment and continuing the flow of the ss DNA through the nanopore, and
(B9) repeating steps (B4)~(B8) until the ss test DNA is stopped by BS1 or BS2, In one embodiment, the ss DNA is a ss test DNA comprising a sample DNA as described supra. Speed bumps comprise one or more nucleotides as defined supra.

A random speed bump pool comprises a collection of speed bumps of a given length that can bind to all sections of the ss test DNA or a fragment thereof (e.g. a sample DNA). Such a given length can be 2, 3, 4, 5, 6, 7, 8, 9, 10, 11, 12, 13, 14, 15, or 16, preferred 10 or less, 8 or less, 6 or less and 4 or less. In one embodiment, the random speed bump pool comprise speed bumps composed of one or more nucleotides selected from the group consisting of universal nucleotides, locked nucleotides, primary nucleotides, modifications thereof, and combinations thereof. Modifications of universal nucleotides, and primary nucleotides include modifications at the nucleobase structures, the backbone structures (e.g. glycol nucleotides, morpholinos, and locked nucleotides) and combinations thereof. In a preferred embodiment, the random speed bump pool comprises oligonucleotides having universal nucleobases which base-pair with all primary nucleobases (A, T, C and G). In another preferred embodiment, the random speed bump pool comprises oligonucleotides having all possible combinations of primary nucleobases. In another preferred embodiment, the random speed bump pool comprises oligonucleotides having all possible combinations of primary nucleobases and universal nucleobases. In another preferred embodiment, the random speed bump pool comprises oligonucleotides having universal nucleotides at designated positions and all combinations of primary nucleobases at the other positions. In another preferred embodiment, the backbone structures of the speed bumps in the random speed bump pool are modified (e.g. glycol nucleotides, morpholinos, and locked nucleotides) at designated position(s), random positions or combinations thereof.

The speed bumps comprise universal nucleobases at designated positions and random primary nucleobases at other positions to lower the total number of possible combinations of primary nucleobases. For example, for a random speed bump pool having 10-base oligonucleotides, the total amount of combinations of the primary nucleobases is $4^{10}=1,048,576$. However, if 4 positions of the 10-base nucleotide are designated to have universal nucleobases only, the total amount of combinations of the primary nucleobases is $4^6=4,096$, which is significantly lower.

In certain embodiments, because the first base pair of the speed bump-test DNA duplex segment may be partially or completely in the nanopore and influence the electrical signals obtained, it is preferred to construct the speed bumps to have a universal nucleotide at the 5' and/or 3° end to normalize the contribution of the first base pair of the speed bump-test DNA duplex segment and makes the signals easier to analyze.

In certain embodiment, the concentrations of one or more speed bumps of a random speed bump pool may be further adjusted to as desired. For example, the concentrations may be about the same for each type of speed bump; and be adjusted such that sufficient ss speed bumps exist to contact the ss test DNA. In one embodiment, because polyG strands bind strongly to polyC strands, polyG and polyC speed bumps will have higher concentrations than speed bumps having other sequences to provide sufficient ss polyG and ss polyC to contact the ss test DNA. In another embodiment, the concentrations of speed bumps and/or nucleotides used to make the speed bumps are adjusted such that each speed bump has about the same affinity to form speed bump-test DNA complex, and no specific speed bumps are significantly more favored than others. In certain embodiments, the concentrations of speed bumps and/or nucleotides used to make the speed bumps are adjusted such that one or more specific speed bumps are significantly more favored than others. For example, the speed bump pool can be constructed to be substantially free of speed bumps that can bind to known segments in the ss test DNA. Therefore, more sequence information obtained will be about the unknown segments and not the known segments in the ss test DNA.

In certain embodiments, step (B5) forms a speed bump-test DNA complex having at least one speed bump-test DNA duplex segment, wherein the speed bump forms a duplex with the ss test DNA segment that is up to 1, 2, 3, 4, 5, 6, 7, 8, 9, 10, 11, 12, 0.3, 14, 15, or 16 basepairs, and is threaded in the nanopore at a first working condition. A working condition includes parameters such as a working temperature (Tw), exposure time, concentration of speed bump and ss test DNA, pH, salt concentration, and other additives and concentration thereof that can affect the formation of speed bump-test DNA complex. Tw is about −10 to about 25° C., about −10 to about 20° C., about −10 to about 15° C., about −10 to about 10° C., about −10 to about 5° C., about −10 to about 0° C., about −10 to about −5° C., about −5 to about 25° C., about −5 to about 20° C., about −5 to about 15° C., about −5 to about 10° C., about −5 to about 5° C., or about −5 to about 0° C., to allow association of relatively short speed bumps (2, 3, 4, 5, 6, 7, 8, 9, 10, 11, 12, 13, 14, 15, or 16 bases) to the ss test DNA. In one embodiment, Tw is about at least 10° C. lower, preferably at least about 20° C. lower than T2. In another embodiment, at Tw, at least about 50% of PB1 and PB2 are in the forms of BS1 and BS2, respectively. In another embodiment, at Tw, at least about 70% of PB1 and PB2 are in the forms of BS1 and BS2, respectively. In another embodiment, at Tw, at least about 90% of PB1 and PB2 are in the forms of BS1 and BS2, respectively.

Exposure time of ss test DNA to speed bumps is about 1 ns or longer, about 10 ns or longer, about 1 μs or longer, about 10 μs or longer, about 1 ms or longer, about 10 ms or longer, about 1 s or longer, or about 5 s or longer to allow sufficient speed bump-test DNA complex to form. Concentrations of the speed bumps are preferably about 100,000 times, 10,000 times, 1,000 times, 300 times, about 200 times, about 100 times, about 50 times, or about 20 times of the concentration of the ss test DNA, or the concentration of the speed bumps is about the same as that of the ss test DNA. The concentrations of the speed bumps are preferably about 1 nM about 100 mM, about 1 nM~about 10 mM, about 1 nM~about 1 mM, about 10 nM~about 100 mM, about 10 nM~about 10 mM, about 10 nM~about 1 mM, about 1 mM~about 10 mM, or about 10 mM~100 mM. The concentration of ss test DNA is about 1 nM~about 100 mM, about 1 nM~about 10 mM, about 1 nM~about 1 mM, about 10 nM~about 100 mM, about 10 nM~about 10 mM, or about 10 nM~about 1 mM. pH is preferably about 6~about 8, or about 7. Salt (e.g. KCl, NaCl, phosphate) concentration is about 1 mM to about 10 M, about 1 mM to about 1 M, about 10 mM to about 10 M, about 10 mM to about 1 M, about 100 mM to about 10 M, or about 100 mM to about 1 M. Other additives that may affect the formation of speed bump-test DNA complex include, without limitation, dextran sulfate and glycerol. Their concentrations may be adjusted to optimize formation of speed bump-test DNA complex.

A working condition further comprises an electric potential of about 0-mV to about 320 mV at a desired polarity. The working condition can be continuously adjusted through the process based on the characteristics of the speed bump binding (e.g. length, nucleotide components, and binding affinity), the nanopore characteristics and the ss test DNA property (e.g. GC content or secondary structure thereof), to optimize the signal quality. Thus, the electric potential can continuously change from for example, −320 mV to +320 mV.

Steps (B4)~(B9) are carried out at a first working condition as described supra. In certain embodiments, the electric potential applied to each step of steps (B4)~(B9) may be the same or different or continuously changing. In certain embodiment, the electric potential for step (B8) may be adjusted to facilitate the dissociation of the speed bump-test DNA duplex segment. In certain embodiment, the electric potential for step (B8) may be applied to move the ss test DNA at a reversed direction compared to the ss test DNA flow direction in step (B6) (forward direction) to move the speed bump-test DNA duplex segment from the constriction area of the nanopore before applying another electric potential to move the DNA at the forward direction to dissociate the speed bump-test DNA duplex segment.

A dwelling time required for a nanopore detector to collect relevant sequence information relates to the nanopore detector and the working condition. In certain embodiments, the dwelling time is at least about 10 μs, at least about 1 ms, at least about 10 ms, at least about 200 ms, at least about 500 ms, at least about 1 s, at least about 2 s, or at about least 5 s. Generally, the longer the dwelling time is, the better the signal quality, and the more sequence information that can be obtained. In certain embodiments, the sequence of up to 5 bases is identified when a speed bump-test DNA duplex segment is stalled in a nanopore. In certain embodiments, the sequence of up to 3 bases is identified when a speed bump-test DNA duplex segment is stalled in a nanopore. In certain embodiments, the sequence of up to 2 bases is identified when a speed bump-test DNA duplex segment is stalled in a nanopore. In certain embodiments, the sequence of 1 bases is identified when a speed bump-test DNA duplex segment is stalled in a nanopore.

As shown in FIG. 4, a ss test DNA comprising bulky structures formed on both ends is locked in a nanopore (steps (B1)~(B4)) and forms speed bump-test DNA complex with multiple speed bumps (step (B5)).

A set of electrical signals of the ss test DNA are obtained each time the ss test DNA is stalled by a speed bump-test DNA duplex segment in the nanopore for a dwelling time, and then the speed bump-test DNA duplex segment dissociates and the ss test DNA moves forward until stalled by the next speed bump-test DNA duplex segment (FIG. 5, the ss test DNA is illustrated to move from Cis side to Trans side). This stall-detect-disassociate-stall process is repeated until the ss test DNA is stopped by the bulky structure of one end. An example of electrical signals obtained is shown in FIG. 8.

In certain embodiments, a random speed bump pool is present mainly on one side of the nanopore (e.g., Cis side as shown in FIG. 5), and the method further comprising:

(B10) applying another electric potential to move the ss test DNA at a reversed direction of the ss test DNA flow in step (B5) until the ss test DNA is stopped by the other bulky structure before the constriction area of the nanopore, (B11) repeating steps (B4)~(B10) at least 1 time, at least 5 times, at least 10 times, at least 15 time, at least 20 time, at least 25 times, at least 30 times, at least 50 times, or at least 100 times and (B12) constructing the ss test DNA sequence by overlapping the collected nucleotide sequence information.

Step (B10) are carried out under a working condition described supra. The electric potential applied can be at a reduced value or a reverse polarity compared to the electric potential applied in step (B4)~(B9) to reverse the flow of the test DNA. The electric potential applied in each step can be the same or different or continuously changing.

Figure 13:
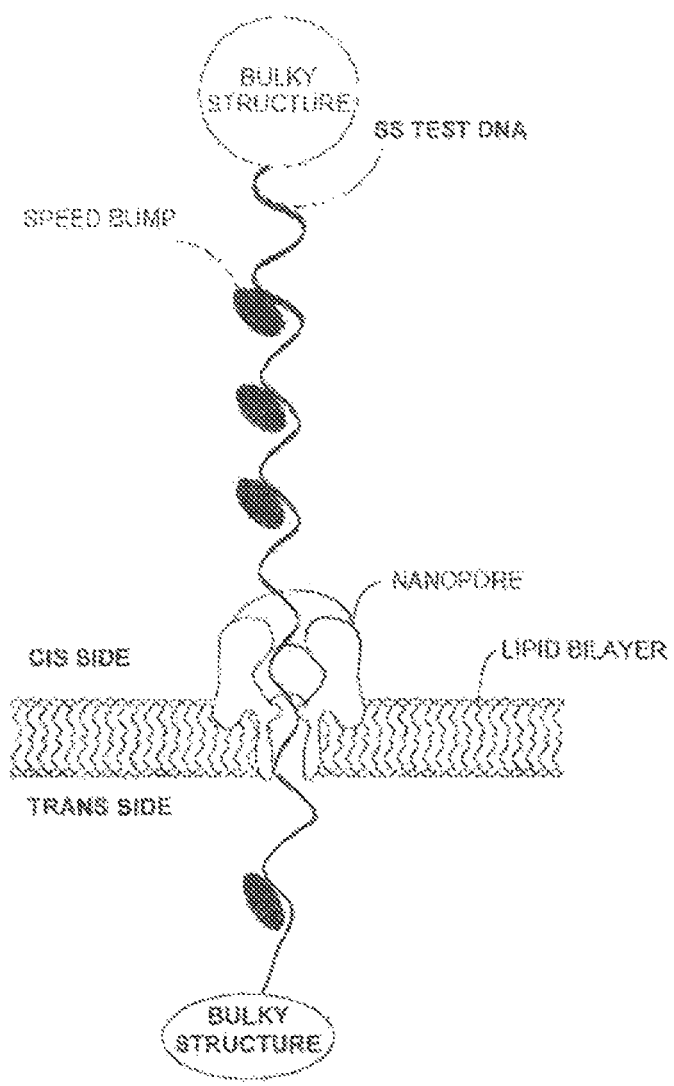
FIG. 13 illustrates a ss test DNA trapped in a nanopore bound with multiple speed bumps on both sides of the nanopore.

In certain embodiments, a random speed bump pool is present in both sides of the nanopore and speed bumps bind to the ss test DNA at the segment exposed to the speed bump pool in both sides of the nanopore (Cis and Trans sides as shown in FIG. 13). The method of identifying a nucleotide sequence of a sample DNA in a ss test DNA described herein further comprising:

(1) repeating steps (B4)~(B8) under a second working condition until the ss test DNA is stopped by the other bulky structure before the constriction area of the nanopore.

(2) repeating steps (B9) and (1) at least 1 time, at least 5 times, at least 10 times, at least 15 time, at least 20 time, at least 25 times, at least 30 times, at least 50 times, or at least 100 times; and (3) constructing the nucleic acid sequence of the sample DNA by overlapping the collected nucleotide sequence information.

The second working condition is a working condition as described supra. The second working condition can have the same or different parameters compared to the first working condition. The electric potential applied in step (1) is at a reduced value or a reverse polarity compared to the electric potential applied in step (B9). The electric potential applied in each step can be the same as applied in the earlier step, or different compared to the earlier step, or continuously changing.

Because a random speed bump pool comprises speed bumps that can bind to random sections of the ss test DNA, each time when the ss test DNA goes from one end stopped by BS1/BS2 to the other end according to the process described herein, speed bumps may bind to different combinations of ss test DNA duplex segments (FIG. 5), and can provide sequence information of different segments in the ss test DNA (FIG. 6). Thus, when step (B8) and/or step (B9) are/is repeated such that sequence information of each and every nucleotide of the sample DNA in the ss test DNA has been obtained, the sample DNA can be constructed by overlapping the collected nucleotide sequence information.

Figure 14:
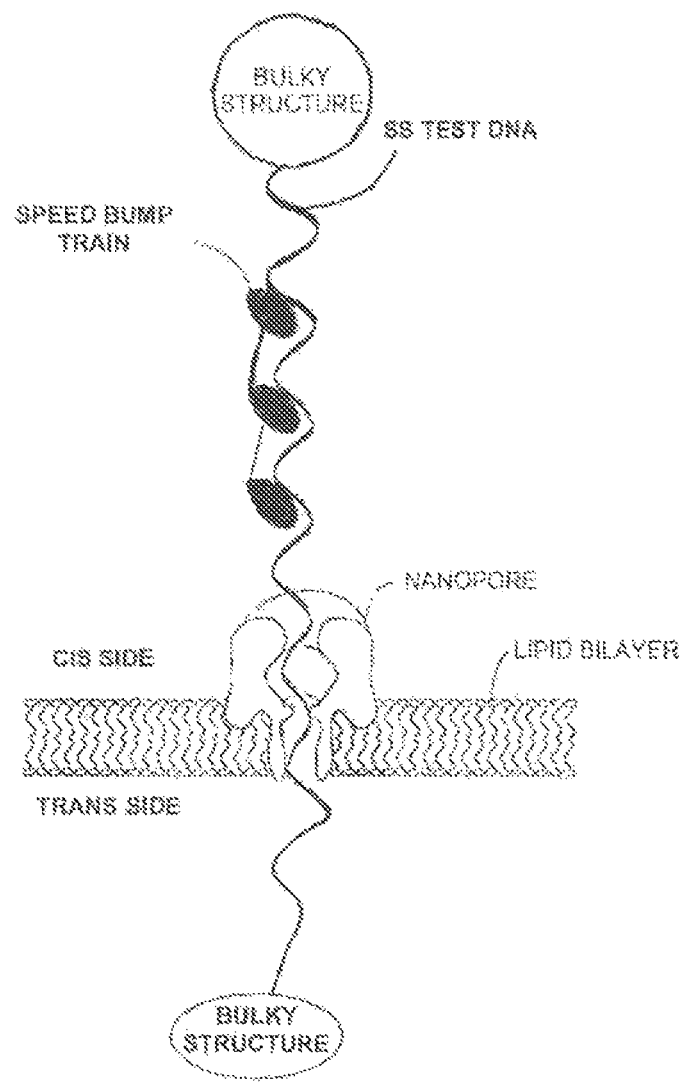
FIG. 14 illustrates contacting a ss test DNA with a speed bump train.

In certain embodiments, more than one speed bump is linked by a non-biding linker (e.g. abasic oligonucleotide) to form speed bump train (FIG. 14) such that the dissociation of each speed bump-test DNA duplex segment will not cause the dissociation of the whole speed bump train from the ss test DNA. In certain embodiments, the non-binding linker is designed to be spaced by about 1 base, about 2 bases, about 3 bases, about 4 bases or about 5 bases. Thus, the gap between known segments shown in FIG. 6 will be more likely to be the same as the length of the linker (e.g. about 1 base, about 2 bases, about 3 bases, about 4 bases or about 5 bases). It will be easier to construct the nucleic acid sequence of the sample DNA in this case.

In certain embodiment, a method described herein wherein:

step (B2) further comprises:

(B2a) obtaining a set of electrical signals when the first bulky structure is stalled inside the nanopore, and characterizing the nucleotide sequence that is in front of the first bulky structure and the first basepair of the first bulky structure, in the flow direction of the ss test DNA, and step (B3) further comprises:

(B3a) obtaining another set of electrical signals when the second bulky structure is stalled inside the nanopore, and characterizing the nucleotide sequence that is in front of the second bulky structure and the first basepair of the second bulky structure, in the flow direction of the ss test DNA.

Figure 15:
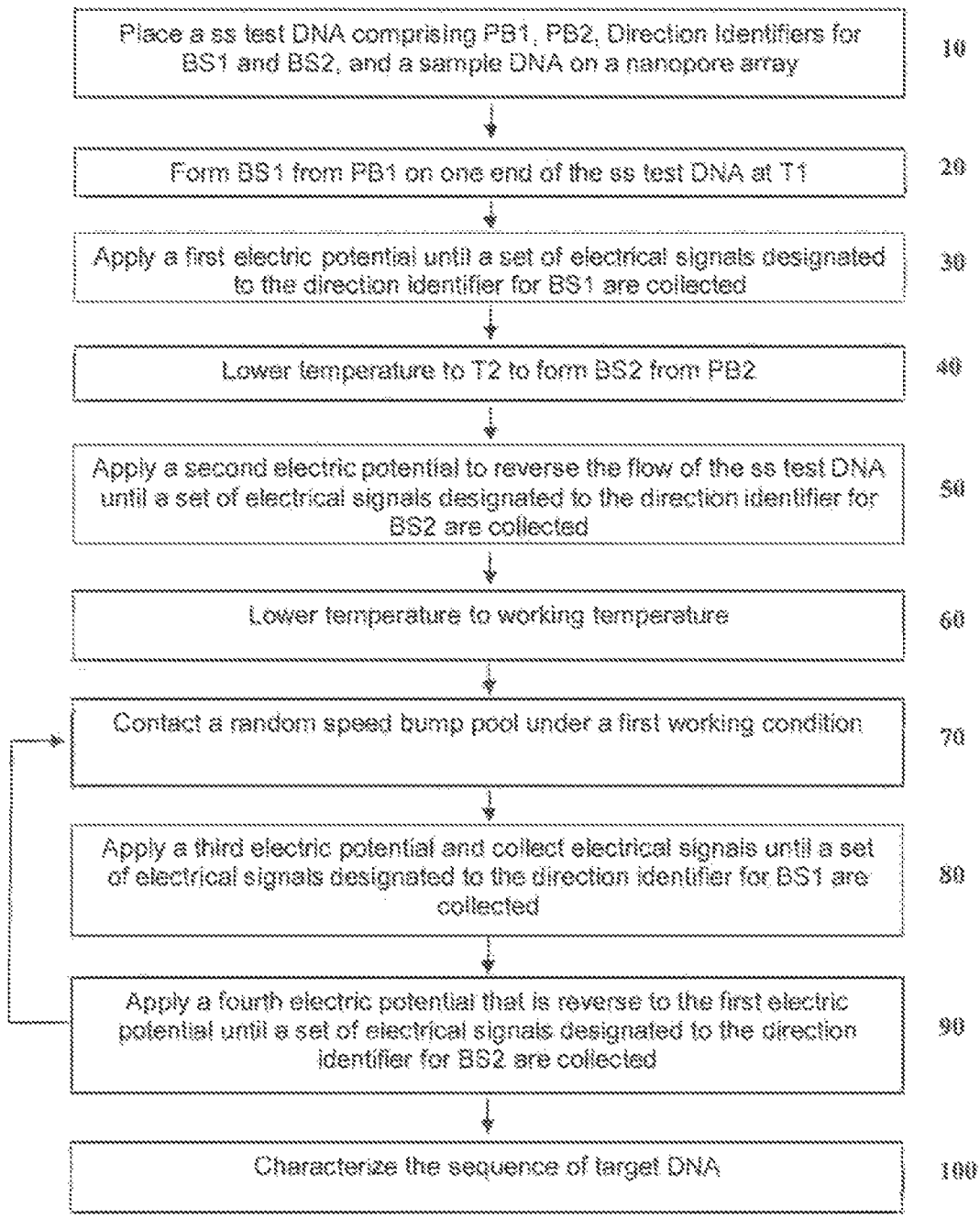
FIG. 15 illustrates a flowchart of a process according to one embodiment of the present disclosure.

In one embodiment, a method as described herein is carried out according to a flowchart shown in FIG. 15. A ss test DNA comprising PB1, PB2, DI1, DI2 and a sample DNA has been constructed and placed on nanopore array (Block 10, FIG. 15). Then BS 1 is formed from PB1 on one end of the ss test DNA at T1 (Block 20, FIG. 15). A first electric potential is applied to thread the ss test DNA through a nanopore until the ss test DNA is stopped by BS1 wherein a set of electrical signals characterizing DI1 are collected (Block 30, FIG. 15). The temperature is then lowered to T2 to form BS2 from PB2 (Block 40, FIG. 15). A second electric potential that is lower than the first electric potential or opposite in polarity to the first electric potential is applied until the ss test DNA is stopped by BS2 wherein a set of electrical signals characterizing DI2 are collected (Block 50, FIG. 15). The temperature is further lowered to Tw (Block 60, FIG. 15), then contact a random speed bump pool with the ss test DNA under a first working condition as described supra to form randomly bound speed bump-test DNA complex (Block 70, FIG. 15). A third electric potential is applied, moving the speed bump-test DNA complex through the nanopore until the ss test. DNA is stalled by a first speed bump-test DNA duplex segment. The ss test DNA is stalled for a dwelling time during which a set of electrical signals are obtained, which will be used to characterize the sequence in front of the first speed bump-test DNA duplex segment and the first base pair of the speed bump-test DNA duplex segment in the flow direction of the ss test DNA. Then the first speed bump-test DNA duplex segment is dissociated and the ss test DNA continues through the nanopore until stopped by the next speed bump-test DNA duplex segment or BS1. A set of electrical signals designated to DI1 are collected when the ss test DNA is stopped by BS1 in the nanopore (Block 80, FIG. 15). Then a fourth electric potential that is at a reduced value or a reverse polarity to the third electric potential is applied until the ss test DNA is stopped by BS2 wherein a set of electrical signals characterizing DI2 are collected (Block 90, FIG. 15). Then the steps in Blocks 70~90 are repeated until sufficient sequence information has been collected to characterize the sequence of the sample DNA.

Detection of an Identifier and Identification of an Identifier in a Test DNA Molecule Another aspect of the invention relates to a method of obtaining sequence information of a ss test DNA molecule as described supra. The method comprises:

(B1) forming a first bulky structure on a first end of the test DNA molecule, (C1) contacting a pool of speed bumps (speed bump pool) with the test DNA molecule to form a speed bump-test DNA molecule complex having at least one speed bump-test DNA molecule segment, (C2) applying an electric potential to flow the speed bump-test DNA molecule complex through a nanopore until a first speed bump-test DNA molecule segment is stalled before the constriction area of the nanopore, (C3) obtaining a first set of electrical signals when the first speed bump-test DNA molecule segment is stalled inside the nanopore for a dwelling time, in the flow direction of the test DNA molecule, (C4) dissociating the first speed bump-test DNA molecule segment and continuing the flow of the molecule through the nanopore, and (C5) repeating steps (C1)~(C4) until the test DNA molecule is stopped by BS1.

In one embodiment, the test DNA molecule is a ss test DNA comprising one or more nucleotides as described supra, and the speed bumps comprise one or more nucleotides as described supra. The ss test DNA comprises PB1 as described supra.

In certain embodiments, step (C1) forms a speed bump-test DNA complex having at least one speed bump-test DNA duplex segment, wherein the speed bump forms a duplex with the test DNA duplex segment that is up to 1, 2, 3, 4, 6, 7, 8, 9, 10, 11, 12, 13, 14, 15, or 16 basepairs.

Steps (C1)~(C5) are carried out at a working condition as described supra.

A dwelling time required for a nanopore detector to collect relevant sequence information is the same as described supra.

In certain embodiment, the method described herein is used to detect an identifier exists in the ss test DNA. An identifier can serve as e.g. direction identifier (e.g. verifying the formation of BS1 and showing the ss test DNA has reached to the end having BS1), reference signal identifier (a reference or calibration read to base line other electrical signals obtained in the same nanopore), sample source identifier (identifying the source of the test DNA), or sample identifier for the test DNA (identifying the test DNA). In certain embodiments, a speed bump pool comprises a first speed bump (FIG. 7) which can bind to a first identifier (identifier 1 in FIG. 7), and is substantially free of other speed bumps that can bind to the ss test DNA (preferably less than 10%, more preferably less than 5%, and most preferably less than 1%). When a ss test DNA comprising identifier 1 contacts the first speed bump, a first speed bump-identifier 1 duplex segment is formed to form a first speed bump-test DNA complex. In the presence of an appropriate electrical field, the first speed bump-test DNA complex goes through a nanopore until stalled by the first speed bump-identifier 1 duplex segment. The nanopore detector obtains a first set of electrical signals. Then the first speed bump-test DNA complex dissociates and the ss test DNA goes through the nanopore until stopped by BS1 at the first end (i.e. in step (C4), the ss test DNA flow through the nanopore smoothly until stopped by BS1 without being stalled again in the nanopore). The nanopore detector will obtain another set of electrical signals when the ss test DNA is stopped by the BS1 structure. Thus, compared to a ss test DNA that does not comprise identifier 1 sequence, the ss test DNA that comprises identifier 1 sequence provides two sets of electrical signals showing that it is stalled twice in the nanopore, while the ss test DNA that does not comprise identifier 1 sequence provides one set of electrical signals showing it is stalled once in the nanopore (by BS1).

In another embodiment, the ss test DNA and/or the speed bumps can be constructed such that the first set of electrical signal obtained in step (C3) is distinctive from a set of electrical signals obtained when a primary nucleotide sequence is detected by the nanopore. For example, the known identifier sequence can comprise one or more nucleotide analogs having isodG and/or IsodC. In front of this identifier sequence is a known reading sequence that would be in the constriction zone of a pore if a speed bump was hybridized to the identifier sequence and stopped in the pore. The reading sequence could comprise IsodC, IsodG and/or abasic positions that do not bind to natural nucleotides. Additionally, both the identifier sequence and the specific antisense speed bump sequence to the identifier would contain appropriate IsodG and IsodC so that only the specific speed bump to the identifier would hybridize to that location. Natural nucleotide speed bumps would not interfere or bind to the IsodG, IsodC-containing identifier sequence and natural nucleotide speed bumps would not interfere with the reading sequence. The resulting identification of the strand in the pore would occur independent of the presence of other natural or man-made nucleotide speed bumps. In this case, the speed bump pool does not have to be substantially free of other speed bumps that can form complex with the ss test DNA. When another speed bump binds to a segment of the ss test DNA other than identifier 1 segment, the first set of electrical signal obtained while the first speed bump-test DNA duplex segment is stalled in the nanopore is distinctive from the other set of electrical signal obtained while the other speed bump-test DNA duplex segments are stalled in the nanopore. Thus, the presence of other speed bumps that can form complex with the ss test DNA does not interfere with the detection of the distinctive signals generated from binding of the first speed bump with identifier 1 of the ss test DNA. The ss test DNA and/or the speed bumps can be further constructed such that no other speed bumps binds to the identifier 1 segment as described supra. Thus, other speed bumps that do not comprise isodG or isodC bases will not bind to the identifier 1 segment.

In another embodiment, the ss test DNA comprises more than one identifier, and the ss test DNA and/or the speed bumps (SBN, N=1, 2, . . . ) that bind to the identifier segments (identifier N) respectively are designed such that when each SBN-identifier N duplex segment is stalled in the nanopore, the set of electrical signal obtained from the nanopore is distinctive from a primary nucleotide sequence and from when other SBN-identifier N duplex segment is stalled in the nanopore. The speed bump pool comprises the speed bumps specific for the identifier(s) that is(are) to be detected, and optionally include speed bumps for other identifiers and/or other speed bumps that can bind to the ss test DNA.

In another embodiment, the identifier that binds to the identifier-specific speed bump and the sequence in front of the identifier in the flow direction of the ss test DNA are both known. Thus, the set of electrical signals obtained in step C3 can also be used to identify the sequence in front of the identifier in the flow direction of the ss test DNA, which can in turn be used to identify of the identifier.

In another embodiment, the method further comprises applying a first electric potential to flow the ss test DNA through a nanopore, and forming a second bulky structure (BS2) on a second end of the ss test DNA under a second condition as described supra. In one embodiment, the temperature of the first condition (T1) is higher than the temperature of the second condition (T2), which is higher than the working temperature Tw. In a preferred embodiment, the temperature of the first condition (T1) is at least 10° C. higher or at least 20° C. higher than the temperature of the second condition (T2), which is at least about 1° C. higher, at least about 5° C. higher, at least about 10° C. higher, at least about 15° C. higher, at least about 20° C. higher, or at least about 25° C. higher than the working temperature Tw.

In certain embodiments, the identifier sequence that is adjacent to the sample DNA is contacted with a first known speed bump (e.g. 2, 3, 4, 5, 6, 7, 8, 9, or 10 bases long), and the sample DNA sequence that is in front of the identifier-speed bump duplex in the first flow direction of the ss test DNA molecule can be identified. Extending the sequence of the known speed bump in the flow direction of the ss test DNA allows identification of longer sequences in the sample DNA. This method comprises the following steps:

(E1) contacting a first known speed bump with the test DNA molecule to form a first known speed bump-test DNA molecule complex having a first known, speed bump-test DNA molecule segment, (E2) applying an electric potential to flow the first known speed bump-test DNA molecule complex through a nanopore until the first known speed bump-test DNA molecule segment is stalled before the constriction area of the nanopore, (E3) obtaining a first set of electrical signals when the first known speed bump-test DNA molecule segment is stalled inside the nanopore for a dwelling time, in the flow direction of the test DNA molecule.

(E4) dissociating the first known speed bump-test DNA molecule segment and continuing the flow of the molecule through the nanopore, (E5) removing the first known speed bumps from the nanopore detector system and reversing the flow of the test DNA until stopped by the bulky structure at the end, and (E6) repeating steps (E1)~(E5) with another known speed bump having a sequence of the first known speed bump plus a known number of bases longer in the flow direction of the test DNA molecule of step (E3), wherein:

E-a) the known number is 1, 2, 3, 4, 5, 6, 7, 8, 9, or 10,

E-b) the known number of bases can be universal bases or bases that are complementary to the bases at the corresponding positions of the sample DNA, and E-c) the condition of step (E4) may be adjusted, e.g. raising the working temperature and/or increasing the electric potential value applied in step (E4) to dissociate the speed bump-test DNA molecule segment successfully Although the method described supra can only identify a sequence of the sample DNA not longer than 15 bases. Such knowledge may facilitate identification/sequencing of the rest of the unknown sequence of the sample DNA using the method described supra (e.g. using a random speed bump pool). Furthermore, the same process can be used to identify a sequence of the sample DNA from another end. Thus, up to 30 bases of an unknown sample DNA can be identified, which will provide a good reference in further identification/sequencing of the Whole sequence of the sample DNA.

Isolation of Sample DNA

Another aspect of the invention relates to a method of isolating a sample DNA comprising:

preparing a ss test DNA using steps (A1)~(A3) as described supra (D1) converting one of the two bulky structure such that the corresponding end of the ss test DNA can go through the nanopore without being stopped, and (D2) applying an electric potential to release the ss target DNA.

In certain embodiments, the ss test DNA further comprises an isolation tag as described supra, and the method further comprises step (D3) after Step (D2):

(D3) attaching the isolation tag to a ligand.

In certain embodiments, wherein the ligand is further attached to a magnetic bead, step (D3) further comprising:

(D3-1) removing the conducting salt solution comprising the released ss test DNA, (D3-2) attaching the isolation tag to a ligand by mixing the released ss test DNA with the ligand attached to a magnetic bead, and (D3-3) isolating the released ss test DNA using conventional isolation methods.

In certain embodiments, the method further comprising step (D4) after step (D3):

(D4) removing the isolated ss test DNA from the bead using conventional methods (e.g. using a basic solution), and (D5) cleaving PB1 and PB2 from the ss test DNA to generate the ss sample DNA.

In certain embodiments, step (D5) further comprising cleaving PB1 and PB2 using endonucleases. In certain embodiments, step (D5) further comprising cleaving PB1 and PB2 at a cleavable site.

In one embodiment, step (D1) further comprises:

(D1-1) changing the temperature of the nanopore to about or higher than the second temperature and lower than the first temperature to convert BS2 to a non-bulky structure.

Sequencing, Identification, Concentration and Isolation of Sample DNAs Using Multiple Nanopore Detectors.

Another aspect of the invention relates to a method of sequencing, identifying, concentrating and isolating of sample DNAs using multiple nanopore detectors. The same method as described herein regarding single nanopore detector can be used to multiple nanopore detectors.

In one embodiment, the multiple nanopores are individually addressable, wherein the electric potential of each nanopore can be individually controlled. The temperature of the nanopore may also be controlled. Thus, the ss test DNA molecules detected in a nanopore can be individually released by carrying out steps (D1)~(D3) on selected nanopores.

For example, in an array of nanopore (numbered as N1, N2, . . . N10), each nanopore has a ss test DNA trapped according to the method described herein, and the individual DNA is numbered DNA1, DNA2, . . . DNA10 in the corresponding nanopores N1, N2, . . . N10. If only DNA1 and DNA 3 are desired to be collected, nanopores N1, N2, . . . N10 can be individually controlled such that only DNA1 and DNA3 are collected (e.g. by applying an electric potential to move DNA1 and DNA3 from nanopores N1 and N3 respectively). In one embodiment, BS2s of DNA1, DNA2, . . . DNA10 are converted to a structure that can go through the nanopores (e.g. PB2s at a temperature about or higher than the second temperature while lower than the first temperature, or cleaved to leave ss structure that can go through the nanopores, respectively). The electric potential of the nanopores N2, N4~N10 are individually controlled such that DNA2, DNA4~DNA10 are released from the nanopores respectively, while DNA1 and DNA3 are still trapped in nanopores N1 and N3, respectively. Then nanopores N1 and N3 are individually controlled to release DNA1 and DNA3, respectively to be collected, concentrated and/or isolated.

The invention is illustrated further by the following examples that are not be construed as limiting the invention in scope to the specific procedures or products described therein.

EXAMPLES

Example 1. PB2 Structure (I)

Figure 16:
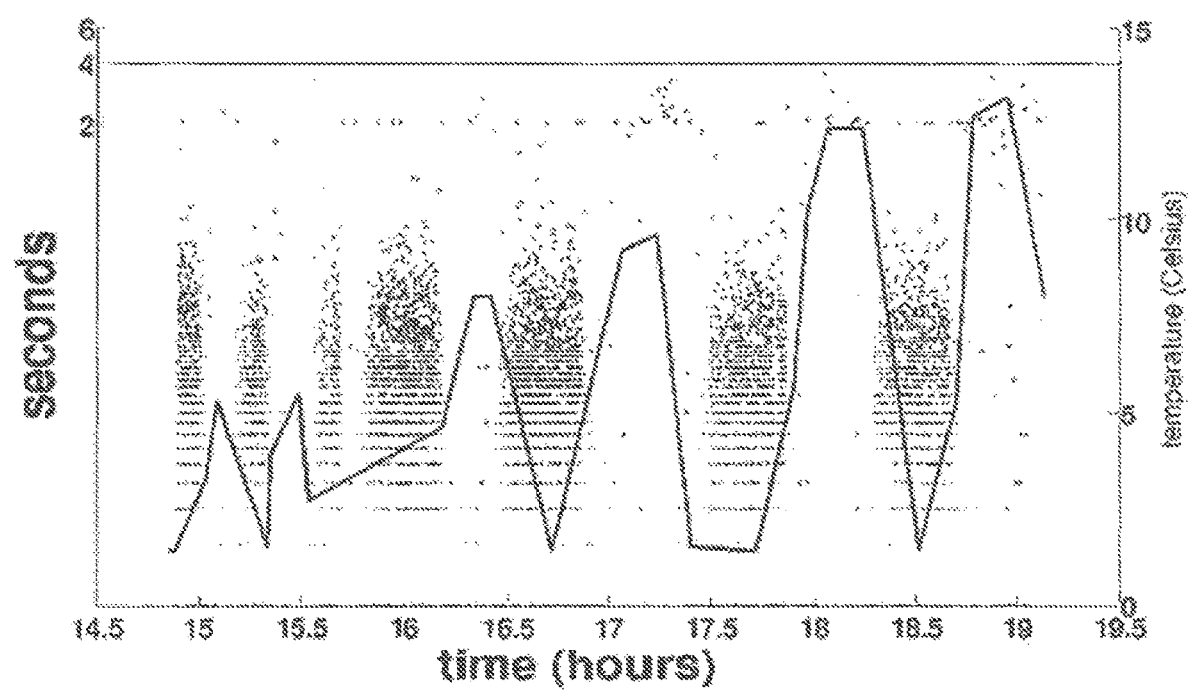
FIG. 16 illustrates the relationship between working temperature and capture of a ss test DNA having BS2-1 on one end and a BS1 on the other end in a nanopore.

A ss test DNA having a BS2 on one end was captured in a nanopore at a temperature lower than T2 and released at a temperature higher than T2 (FIG. 16).

The BS2 (BS2-1) was a DNA 5-base duplex hairpin structure formed from a PB2 having a sequence of 5'-CCCCC CCCCC TTATA CCCCT ATAA-3' (SEQ ID NO. 1, PB2-1). BS2-1 had melting temperature of about 15° C., and a ΔG of about −0.96 kcal/mol at 5° C. according to the simulation using UNAFOLD program. This moderately low ΔG indicated that BS2-1 had a relatively low binding energy.

In FIG. 16, the solid line showed the change in temperature from 2° C. to 14° C. The dots represented individual DNA captures, meaning that PB2-1 formed BS2-1 at the corresponding temperature and was captured in the nanopore. The captures were present when the temperature was about or lower than T2 (about 5° C.), indicating that BS2-1 was formed from PB2-1 and the DNA was stalled in, the nanopore. The capture of the DNA disappeared when the temperature increased to about 5~10° C. over T2, indicating that BS2-1 melted and was no longer stalled in the nanopore.

Thus, PB2-1 formed BS2-1 which stopped the ss DNA in the pore at a temperatures about 10° C. lower than its melting temperature. This may be due to the relatively low ΔG BS2-1 had. Thus, the DNA duplex structure in BS2-1 was relatively easy to dissociate in the nanopore. Thus, a BS2 having a higher ΔG may be more difficult to destruct and may provide longer dwelling time at the nanopore at a temperature closer to the melting temperature of the BS2.

Example 2. PB1 and PB2 Structure (II)

A PB1 forms a BS1 at a first temperature (T1) that is higher than the second temperature (T2) at which a BS2 is formed from a PB2. T2 is higher than a working temperature (Tw). In this example, Tw is below room temperature. Thus, PB1 is designed to have a relative long DNA duplex segment (either in a DNA duplex with an anti-sense DNA segment, or in a hairpin structure) such that the desired melting temperature of the relative long DNA duplex segment is achieved.

PB2 is designed to have a lower melting temperature and a high binding energy (ΔG=about −1~−5 kcal/mol, about −4~−6 kcal/mol, about −4~−5 kcal/mol, about −4.5 kcal/mol, or about −4.0 kcal/mol at the working condition). A molly bolt or branched molecule has been designed to provide a BS2 having low T2 while not easily dissociated at the working condition.

An example of PB1 has a sequence of 15 bases and a 4 base A loop; 5'-CGTCT AGCGT TGCCG AAAAC GGCAA CGCTA GACG-3' (SEQ ID NO. 2, PB1-1). This sequence has a melt temperature of 91.4° C. in 1 M KCl, and 1 μM sequence concentration according to the simulation using UNAFOLD program.

An example of PB2 has a sequence of 5'-GACCC TGCCC CCAGC TTTCC CCAAA CGTCA AAAAA-3' (SEQ ID NO. 3, PB2-2) and the formed BS2-2 is a 3 stem, 3 duplex, 2 loop molecule as shown below according to the simulation using UNAFOLD program:

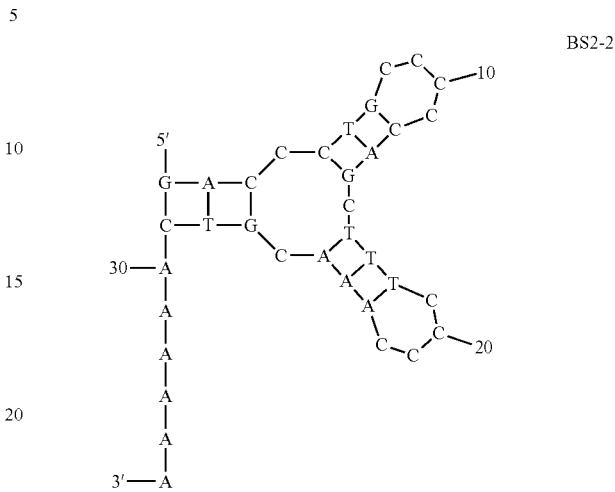

The following characteristics of the BS2-2 were provided using UNAFOLD program:
ΔG=−4.5140 kcal/mol at 5° C. (100% folded),
ΔH=−67.90 kcal/mol,
ΔS=−227.9 cal/(K·mol) and
Tm=24.8083° C.

Figure 17:
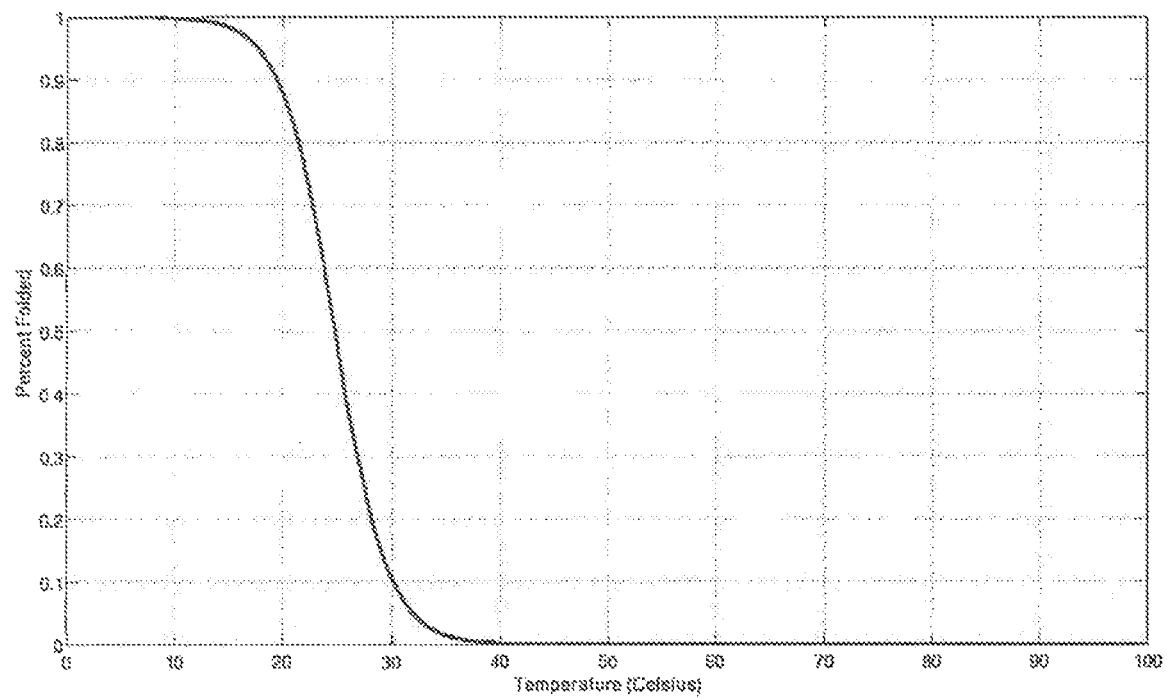
FIG. 17 illustrates a melting curve of an exemplary bulky structure (BS2-2).

A calculated melting curve of BS2-1 was obtained using nearest neighbor basis and shown in FIG. 17. This melting curve illustrates that at above 30° C. about 90% of the structures are linear (PB2-2) and at below 20° C. about 90% of the structures form BS2-2. Such a steep melting curve shows well controlled bulky structure formation of BS2-2, which is highly desired. The ΔG of BS2-2 at 5° C. is −4.5 kcal/mol, which indicates a stronger binding affinity than the 5 base hairpin molecule BS2-1 in Example 1.

Example 3. Stalling DNA by 4-Base Duplex Segments

This example illustrates a 4-baser duplex segment stalled the ss test DNA in a nanopore for a dwelling time sufficient to obtain desired sequence information.

The test DNAs were the following:
A test DNA was formed by self-hybridization of DNA-1: 5'-CCCCC CCCCC GCGC-3' (SEQ ID NO. 4). DNA-1 was dissolved in biology grade water, heated to 90 CC and then left to cool to room temperature for self-hybridization. A DNA-1 molecule hybridize with another DNA-1 molecule to form a self-hybridized DNA-1 structure having a 4-base GCGC duplex segment at the 3' ends and two overhanging ss 10-C tails at the 5' ends thereof. At the working condition, the self-hybridized DNA-1 structure entered a nanopore with one of the two overhanging ss 10-C tails, stalled in the nanopore by the 4-base duplex segment at the 3' end for a dwelling time, and then when the 4-base duplex segment dissociated, the self-hybridized DNA-1 structure was converted to two ss DNA-1 molecules which went through the nanopore like ss test DNAs. Thus, when flowing through a nanopore, the self-hybridized DNA-1 structure simulated a ss test DNA having a 4-base duplex segment formed by a speed bump and the ss test DNA.

Another test DNA, self-hybridized DNA-2 structure, was formed by self-hybridization of DNA-2: 5'-TTTTT TTTTT GCGC-3' (SEQ ID NO. 5) using the same process described supra regarding the formation of the self-hybridized DNA-1. The self-hybridized DNA-2 structure had a 4-base GCGC duplex at the 3' ends and two overhanging ss 10-T tails at the 5' ends.

Another test DNA was streptavidin-DNA-3 complex formed by incubation of DNA-3: 5'-TTTTT TTTTT TTTTT TTTTT TTTTT TTTTT TTTTT TTTTT TTTTT-biotin-3' (SEQ ID NO. 6) and streptavidin at a condition described below. When flowing through a nanopore under a electric potential, streptavidin-DNA-3 complex stalled in the nanopore until the electric potential was changed/reversed. Thus, streptavidin-DNA-3 complex served as a positive control showing that the nanopore detector system was working properly. The dwell time of this molecule was long, represented by the points at the far right side of the x-axis (time) in FIG. 18.

The working condition was 20 mM HEPES buffer and 1 M KCl at 0° C. The electric potential applied was about 128 mV.

The nanopores were created from 10 ng/mL alpha hemolysin deposited onto the surface of a bilayer at a final concentration of 0.2 ng/mL and with the application of electrical stimulus as described in US Application Publication. No. 2011/0193570. The bilayers were created with the painting method from 10 mg/mL of DPhPC in Decane across the essentially planar AgCl electrode on a Teflon surface as described in US Application Publication 2011/0193570.

Figure 18:
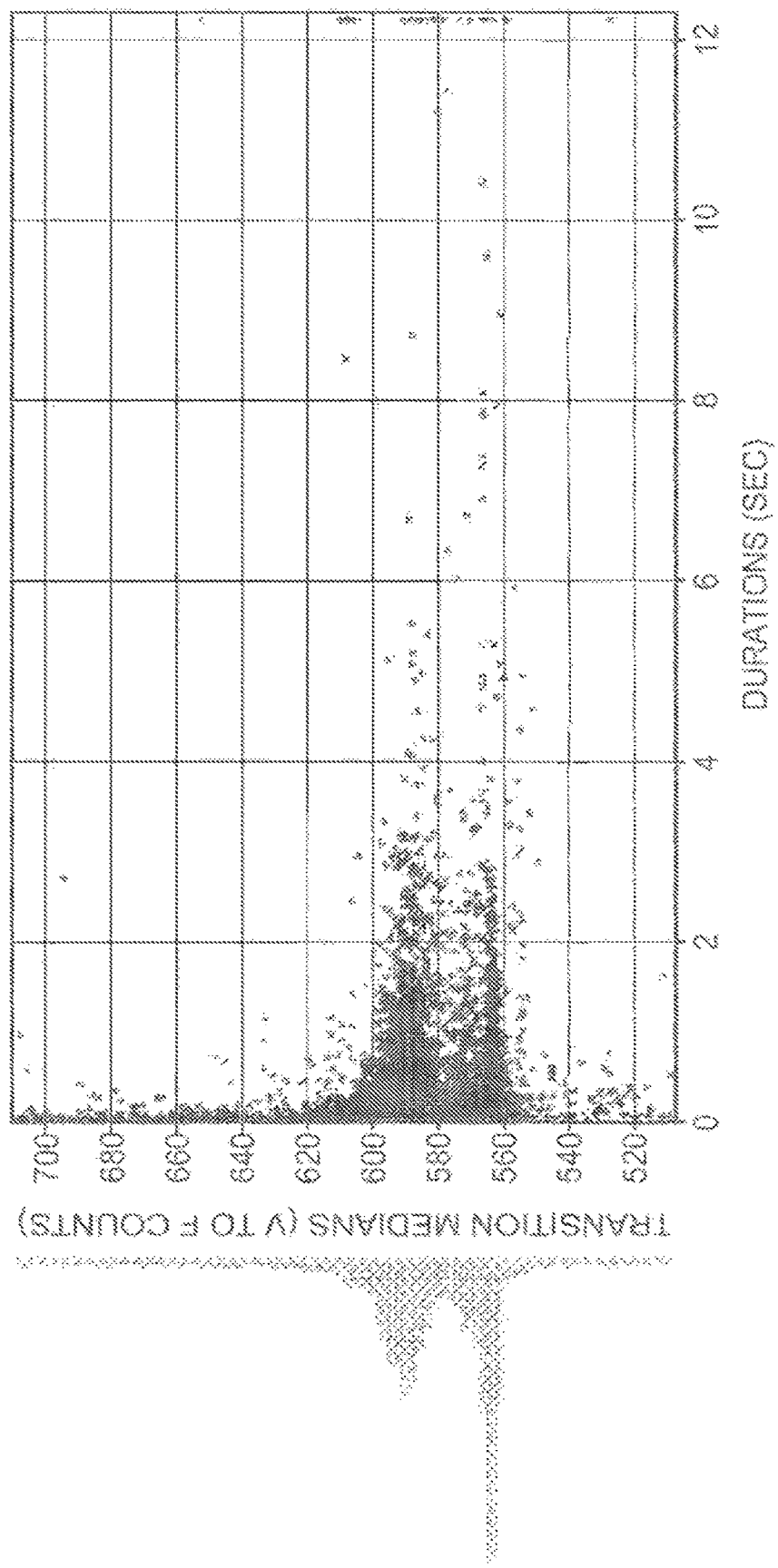
FIG. 18 illustrates the relationship between electric potential applied and dwelling time of speed hump-test DNA duplex in a nanopore.

Self-hybridized DNA-1 (2 µM self-hybridized DNA-2 (2 µM), DNA-3 (2 µM), and streptavidin (1 µM) were incubated with multiple nanopores constructed as described supra for about 2 h at the working condition described supra in this example. An electric potential of about 128 mV was applied to the nanopore and electrical signals were collected and shown in FIG. 18. FIG. 18 showed that the 4-base duplex segments were able to stall DNA-1 and DNA-2 in the nanopore for a dwelling time of about 100 ms to 200 ms.

These data showed that speed bumps as short as 4 bases worked to stall a ss test DNA long enough to obtain relevant sequence information.

Example 4. Stalling DNA by 6-Base Random Speed Bump Pool

This example illustrates a 6-base random speed bump pool successfully bound to, stalled in a nanopore detector and dissociated from a test DNA.

In this example, the ss test DNA was ss female genomic DNA. The random speed bump pool comprised hexamer DNA oligonucleotides having all combinations of the primary DNA nucleotides, which was purchased from Invitrogen.

The working condition was 20 mM HEPES buffer and 1 M KCl at 0° C. The electric potential applied was about 128 mV.

The nanopores were created from 10 ng/mL alpha hemolysin deposited onto the surface of a bilayer at a final concentration of 0.2 ng/mL and with the application of electrical stimulus as described in US Application Publication. No. 2011/0193570. The bilayers were created with the painting method from 10 mg/mL, of DPhPC in Decane across the essentially planar Aga electrode on a Teflon surface as described in US Application Publication. No. 2011/0193570.

The ss test DNA (1 µM) was incubated with the 6-base random speed bump pool (100 µM) were incubated with multiple nanopores constructed as described supra for about 2 h at the working condition described supra in this example. An electric potential of about 128 mV was applied to the nanopore and electrical signals were collected. The signals showed that the 6-base random speed bump pool was able to bind to the ss test DNA, stall the ss test DNA in the nanopore long enough to obtain relevant sequence information, and dissociate from the ss test DNA as described herein.

The invention claimed is:

1. A method for sequencing a molecule comprising a plurality of nucleotides or nucleotide analogs, the method comprising:
    applying a first electric potential having a first polarity across an array of nanopore detectors, each nanopore detector comprising a pair of electrodes, a membrane disposed between the pair of electrodes, and a nanopore disposed in the membrane;
    threading a plurality of molecules through the array of nanopore detectors in a first direction based on the first polarity of the applied first electric potential;
    measuring a first electrical signal in each nanopore detector as the molecule is threaded through the nanopore in the first direction;
    applying a second electric potential having a second polarity across the array of nanopore detectors, wherein the second polarity is opposite the first polarity;
    threading the plurality of molecules through the array of nanopore detectors in a second direction based on the second polarity of the applied second electrical potential, wherein the second direction is opposite the first direction;
    applying a third electrical potential across the array of nanopore detectors, wherein the third electrical potential has a polarity that is the same as the polarity of the first electrical potential;
    threading the plurality of molecules through the array of nanopore detectors in the first direction based on the polarity of the third electrical potential;
    measuring a second electrical signal in each nanopore detector as the molecule is threaded through the nanopore in the first direction as a result of the application of the third electrical potential;
    determining a sequence for each molecule based on the first electrical signal and the second electrical signal; and
    applying a fourth electrical potential across the array of nanopore detectors, wherein the fourth electrical potential has a polarity that is the same as the polarity of the first electrical potential, wherein the fourth electrical potential has a magnitude that is greater than the first electrical potential that is configured to advance the molecule past a speed bump that is slowing or stalling the threading of the molecule through the nanopore.

2. The method of claim 1, wherein each molecule has a first end comprising a first bulky structure.

3. The method of claim 2, wherein the first end is the trailing end of the molecule and the first bulky structure is configured to prevent the molecule from passing completely through the nanopore when the molecule is threaded through the nanopore in the first direction.

4. The method of claim 2, wherein each molecule has a second end comprising a second bulky structure.

5. The method of claim 4, wherein the second end is the leading end of the molecule and the second bulky structure is configured to prevent the molecule from passing completely through the nanopore when the molecule is threaded through the nanopore in the second direction.

6. The method of claim 2, wherein the first end is the leading end of the molecule and the second first structure is configured to prevent the molecule from passing completely through the nanopore when the molecule is threaded through the nanopore in the second direction.

7. The method of claim 1, wherein each molecule comprises a plurality of speed bumps located along a length of the molecule, wherein the plurality of speed bumps are configured to slow or stall the threading of the molecule through the nanopore.

8. The method of claim 1, wherein the first electrical potential, the second electrical potential, and the third electrical potential have a magnitude that is less than the magnitude of the fourth electrical potential.

9. The method of claim 1, wherein the first electrical potential, the second electrical potential, and the third electrical potential have a magnitude that is too low to reliably advance the molecule past a speed bump that is slowing or stalling the threading of the molecule through the nanopore.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: duplex hairpin structure

<400> SEQUENCE: 1
cccccccccc ttataccccct ataa                                        24

<210> SEQ ID NO 2
<211> LENGTH: 34
<212> TYPE: DNA
<213> ORGANISM: Artificial Sequence
<220> FEATURE:
<223> OTHER INFORMATION: duplex hairpin structure

<400> SEQUENCE: 2
cgtctagcgt tgccgaaaac ggcaacgcta gacg                              34

<210> SEQ ID NO 3
<211> LENGTH: 35
<212> TYPE: DNA
<213> ORGANISM: Artificial Sequence
<220> FEATURE:
```

```
<223> OTHER INFORMATION: multi-hairpin structure

<400> SEQUENCE: 3
gaccctgccc ccagctttcc ccaaacgtca aaaaa                              35

<210> SEQ ID NO 4
<211> LENGTH: 14
<212> TYPE: DNA
<213> ORGANISM: Artificial Sequence
<220> FEATURE:
<223> OTHER INFORMATION: self-hybridizable structure

<400> SEQUENCE: 4
cccccccccc gcgc                                                     14

<210> SEQ ID NO 5
<211> LENGTH: 14
<212> TYPE: DNA
<213> ORGANISM: Artificial Sequence
<220> FEATURE:
<223> OTHER INFORMATION: self-hybridizable structure

<400> SEQUENCE: 5
tttttttttt gcgc                                                     14

<210> SEQ ID NO 6
<211> LENGTH: 40
<212> TYPE: DNA
<213> ORGANISM: Artificial Sequence
<220> FEATURE:
<223> OTHER INFORMATION: 3'-biotinylated structure

<400> SEQUENCE: 6
tttttttttt tttttttttt tttttttttt tttttttttt                         40
```